US012617702B2

(12) United States Patent
Portillo Hahnefeld et al.

(10) Patent No.: US 12,617,702 B2
(45) Date of Patent: May 5, 2026

(54) METHOD FOR PRODUCING BIOMASS FROM A MICROALGAE

(71) Applicant: UNIVERSIDAD DE LAS PALMAS DE GRAN CANARIA, Las Palmas de Gran Canaria (ES)

(72) Inventors: Agustín Portillo Hahnefeld, Telde (ES); Antera Martel Quintana, Telde (ES); Juan Luis Gómez Pinchetti, Telde (ES)

(73) Assignee: Universidad de Las Palmas de Gran Canaria, Las Palmas de Gran Canaria (ES)

( * ) Notice: Subject to any disclaimer, the term of this patent is extended or adjusted under 35 U.S.C. 154(b) by 464 days.

(21) Appl. No.: 17/793,116

(22) PCT Filed: Jan. 15, 2021

(86) PCT No.: PCT/ES2021/070017
§ 371 (c)(1),
(2) Date: Jul. 15, 2022

(87) PCT Pub. No.: WO2021/144491
PCT Pub. Date: Jul. 22, 2021

(65) Prior Publication Data
US 2023/0061001 A1 Mar. 2, 2023

(30) Foreign Application Priority Data
Jan. 17, 2020 (ES) ............................... ES202030030

(51) Int. Cl.
| | | |
|---|---|---|
| *C02F 3/32* | (2023.01) | |
| *C12M 1/00* | (2006.01) | |
| *C12N 1/066* | (2026.01) | |
| *C12N 1/125* | (2026.01) | |

(52) U.S. Cl.
CPC ............. *C02F 3/322* (2013.01); *C12M 21/02* (2013.01); *C12N 1/066* (2013.01); *C12N 1/125* (2021.05)

(58) Field of Classification Search
CPC .......... C12N 1/125; C12N 1/066; C12N 1/12; C02F 3/322; C02F 2103/08; C12M 21/02
See application file for complete search history.

(56) References Cited

U.S. PATENT DOCUMENTS

| | | | |
|---|---|---|---|
| 2010/0010088 A1* | 1/2010 | Chilton .................. | A23K 50/10 |
| | | | 426/601 |
| 2012/0171733 A1* | 7/2012 | Im ........................... | C12N 1/12 |
| | | | 435/166 |
| 2017/0058254 A1* | 3/2017 | Schulz-Raffelt ............................ | |
| | | | C12Y 207/12001 |

FOREIGN PATENT DOCUMENTS

| | | |
|---|---|---|
| CN | 103881923 A | 6/2014 |
| CN | 105861312 A | 8/2016 |
| EP | 2478089 B1 | 5/2019 |
| WO | 2012135150 A2 | 10/2012 |

OTHER PUBLICATIONS

Rodriguez Leon, C. Search for marine natural products with cytotoxic activity. Universidad de Las Palmas de Gran Canaria. Jul. 2020. [online], [retrieved on Nov. 14, 2024]. Retrieved from the Internet <URL: https://accedacris.ulpgc.es/bitstream/10553/74363/2/0767079_00000_0000.pdf> (Year: 2020).*
Han, KY et al. A re-investigation of Sarcinochrysis marina (Sarcinochrysidales, Pelagophyceae) from its type locality and the descriptions of Arachnochrysis, Pelagospilus, Sargassococcus and Sungminbooa genera nov. Protist. 2018. 169: 79-106. (Year: 2018).*
Ledda, C et al. Utilization of centrate from wastewater treatment for the outdoor production of Nannochloropsis gaditana biomass at pilot-scale. Algal Research. 2015. 12: 17-25. (Year: 2015).*
"Deliverable 6.1 Characterization of Microalgae Strains for Agricultural/Aquaculture Applications at Large Scale", 2018, Sustainable Algae Biorefinery for Agriculture and Aquaculture, EU Commission SABANA project under Grant Agreement 727874, pp. 1-67.
Magnotti et al., "Using residual water from a marine shrimp farming BFT system. part I: nutrient removal and marine microalgae biomass production", Aquaculture Research, 2016, pp. 2435-2443, vol. 47.
Romero Villegas et al., "Outdoor production of microalgae biomass at pilot-scale in seawater using centrate as the nutrient source," Algal Research, 2017, pp. 538-548, vol. 25.
Romero-Villegas et al., "Utilization of centrate for the outdoor production of marine microalgae at pilot-scale in flat-panel photobioreactors," Journal of Biotechnology, 2018, pp. 102-114, vol. 284.
Roux et al., "An Overview of Microalgae Lipid Extraction in a Biorefinery Framework," Energy Procedia, 2017, pp. 680-688, vol. 112.
Sepúlveda et al., "Utilization of centrate for the production of the marine microalgae Nannochloropsis gaditana," Algal Research, 2015, pp. 107-116, vol. 9.
Shi et al., "Application of a prototype-scale Twin-Layer photobioreactor for effective N and P removal from different process stages of municipal wastewater by immobilized microalgae", Bioresource Technology, 2014, vol. 154, pp. 260-266.

* cited by examiner

*Primary Examiner* — David W Berke-Schlessel
*Assistant Examiner* — Susan E. Fernandez
(74) *Attorney, Agent, or Firm* — The Webb Law Firm

(57) ABSTRACT

A method for producing biomass from a microalgae includes culturing the microalgae in an effluent diluted in seawater. A method for bioremediating an effluent includes culturing a microalgae in the effluent diluted in seawater. The microalgae is at least one of a strain of the genus *Nodularia,* a strain of the genus *Chrysoreinhardia,* a strain of the genus *Halochlorella,* or combinations thereof. At the beginning of culturing, the diluted effluent exhibits concentrations of total nitrogen (N) in the range of 30-150 mg/l and concentrations of total phosphorus (P) in the range of 1-15 mg/l. The N/P quotient is in the range of 5-40.

20 Claims, 3 Drawing Sheets

METHOD FOR PRODUCING BIOMASS FROM A MICROALGAE

CROSS-REFERENCE TO RELATED APPLICATIONS

This application is the United States national phase of International Application No. PCT/ES2021/070017 filed Jan. 15, 2021, and claims priority to Spanish Patent Application No. P202030030 filed Jan. 17, 2020, the disclosures of which are hereby incorporated by reference in their entirety.

BACKGROUND

Field

The invention relates to the use of effluents from wastewater treatment as a source of nutrients for culturing microalgae.

Description of Background Art

Water contamination is one of the most serious problems for our planet, which, together with the limitations in the availability of water in large areas of the planet, can result in a danger to the health of the population. Currently, all wastewater in developed countries is treated in main treatment plants and, subsequently, the discharge thereof into the sea or rivers is allowed, after a series of complex purification treatments. In a wastewater purification process, the sludge accumulated in an initial filtration phase is treated in anaerobic digesters, to reduce the volume and toxicity thereof. This process mainly produces methane, dry sludge and reject water (effluent). Methane is reused as a source of energy in many treatment plants, dry sludge is generally reused as peat, but the fraction of reject water (effluent) returns to the treatment plant to be treated. This type of water is a big problem, since this effluent exhibits a very significant contaminant load, with high concentrations of nitrate, ammonium and phosphate, BOD and COD, as well as bacteria. The incorporation of this type of water in the flow of a wastewater treatment plant causes a severe problem since the effluent alters all the chemical parameters of the treated water. For this reason, in some treatment plants it is stored until favourable conditions are found for the purification thereof. The composition of the effluent varies considerably from one region to another and is always a function of the origin of the sludge being treated. Its high contaminant load, high concentrations of ammonia and bacteria, as well as numerous infectious agents harmful to the population, animals and plants are also evident. Currently, the removal of contaminants from this water is very costly and time consuming. However, this reject water (effluent) can be used as a source of nutrients for culturing microalgae, since it contains nutritional requirements of algae in an adequate proportion, in addition to a much lower bacterial concentration since the effluent is typically obtained under anaerobic conditions. In addition to being useful in the purification of this wastewater, the use of an effluent as a source of nutrients for culturing microalgae leads to the production of biomass with economic benefit. This biomass can be used as a source for a fertiliser, pesticide, feed, feed for fish, biofuel, jet fuel, biodiesel, pigment, surfactant, cosmetic, pharmaceutical agent, health supplement, or the manufacture of bioplastic. The use of wastewater treatment effluent as a source of nutrients for the production of microalgal biomass has been shown to be effective in many recent studies. The eukaryotic microalgae most frequently used in wastewater treatment are of the genus *Chlorella, Scenedesmus, Muriellopsis, Botryococcus* and *Nannochloropsis* and also the cyanobacterium *Phormidium bohneri*. However, the optimal effluent concentration that can be used as a source of nutrients in the production of microalgae has to be individually studied in each case. It must be taken into account that the effluent concentration varies widely from one treatment plant to another. Therefore, the growth rate and robustness of microalgal cultures are not in all cases sufficient to be efficient in water purification.

Therefore, detecting, bioprospecting, identifying and characterising strains continues to be one of the fundamental objectives in this type of study, to search for the highest production rates, the ability to remove nutrients, resistance to pathogens and bacteria, and the optimisation of the biomass obtained.

SUMMARY

The inventors have found that the strains of eukaryotic microalgae *Chrysoreinhardia giraudii* BEA_IDA_0071B and *Halochlorella rubescens* BEA_IDA_0072B, and strains of cyanobacteria *Nodularia spumigena* BEA_IDA_0069B (according to a previous taxonomic study, the strain BEA_IDA_0069B had been identified with a species of *Anabaena* sp.) and *Nodularia harveyana* BEA_IDA_0070B (according to a previous taxonomic study, the strain BEA_IDA_0070B had been identified with a species of *Dolichospermum* sp.) exhibit significant rates of biomass production and removal of contaminants when cultured in a culture medium prepared by diluting an effluent from the Salto del Negro treatment plant (Gran Canaria, Spain) in seawater at 0.5%, in such a way that, in the diluted effluent, concentrations of N—total nitrogen (ammonium and nitrate)—of 106 mg/l and concentrations of P—total phosphorus (orthophosphate)—of 3.75 mg/l are achieved. These concentrations result in an N/P quotient of 31.3.

Thus, a first aspect of the invention relates to a method for producing biomass from a microalgae, wherein the method comprises culturing the microalgae in an effluent diluted in seawater, wherein the microalgae is selected from the group consisting of a strain of *Nodularia*, a strain of *Chrysoreinhardia*, a strain of *Halochlorella*, and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range.

A second aspect the invention relates to a method for the bioremediation of an effluent, wherein the method comprises culturing a microalgae in the effluent diluted in seawater, wherein the microalgae is selected from the group consisting of a strain of the genus *Nodularia*, a strain of the genus *Chrysoreinhardia*, a strain of the genus *Halochlorella*, and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range.

An additional aspect of the invention relates to a method for producing a biomass extract of a microalgae, wherein the method comprises culturing the microalgae in an effluent diluted in seawater, wherein the microalgae is selected from the group consisting of a strain of the genus *Nodularia,* a strain of the genus *Chrysoreinhardia,* a strain of the genus *Halochlorella,* and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range;

harvesting the biomass from the microalgae by filtration; subjecting the microalgal biomass to a cellular breakage method, and obtaining the extract resulting from cellular breakage.

Another aspect of the invention relates to a method for producing a processed material from microalgal biomass, wherein the method comprises: (a) producing microalgal biomass according to a method according to the first aspect of the invention, and (b) producing a processed material from microalgal biomass.

A last aspect of the invention relates to a microalgal biomass obtainable by means of the method for producing biomass from a microalgae of the first aspect of the invention.

In addition, the invention relates to the use of a microalgal biomass according to the present invention to produce a processed material, wherein the processed material is selected from the group consisting of a fertiliser, pesticide, feed, feed for fish, biofuel, jet fuel, biodiesel, pigment, surfactant, cosmetic, pharmaceutical agent, health supplement, or bioplastics.

DETAILED DESCRIPTION

Figure 1:
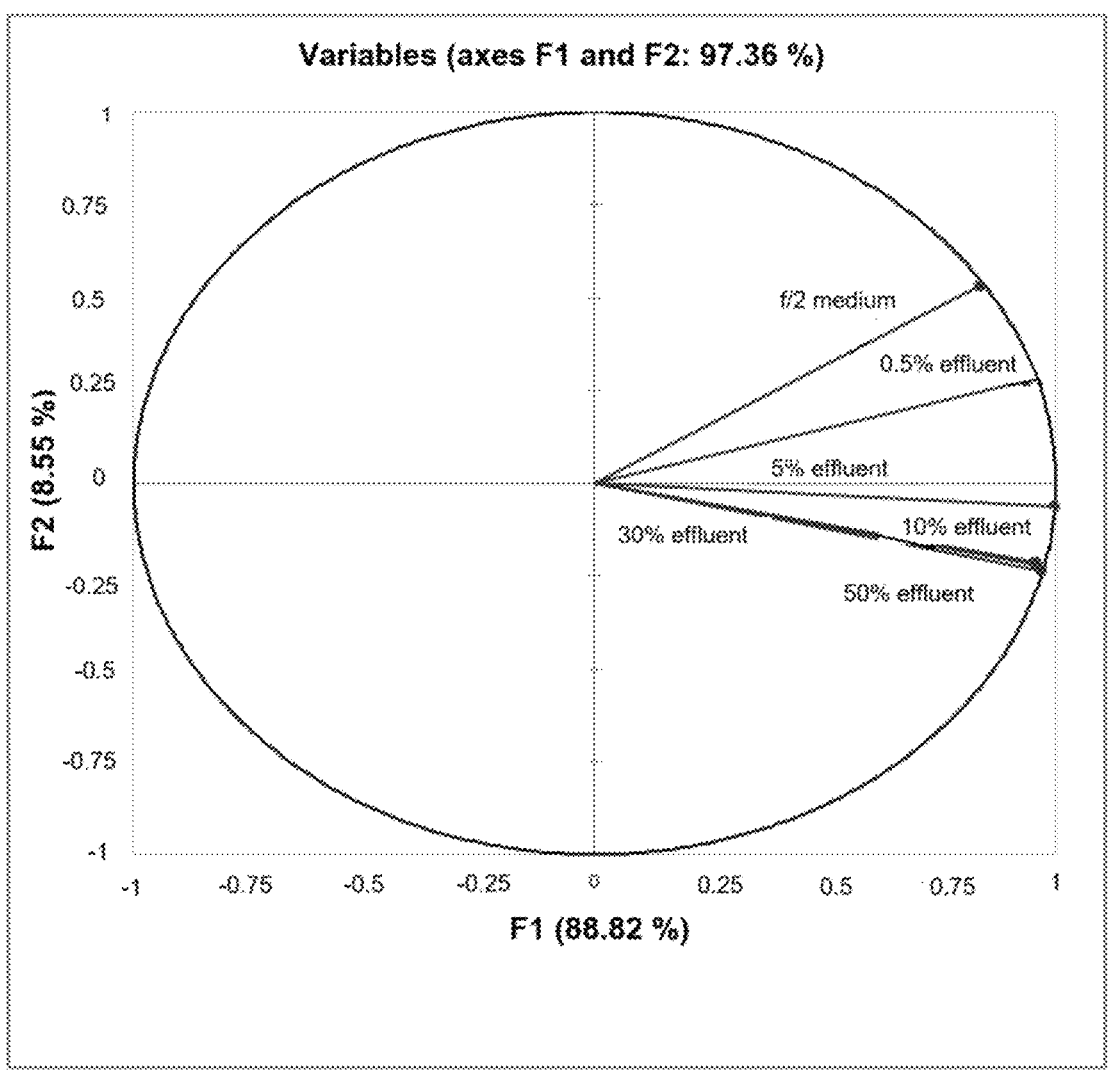
FIG. 1. Principal components analysis among the main parameters (nutrient composition, N/P quotient, bacterial activity, salinity, pH, conductivity, dry weight and CDOM) in f/2 medium and in the different dilution percentages of the effluent.

As explained above, the inventors have found that strains of eukaryotic microalgae *Chrysoreinhardia giraudii*

BEA_IDA_0071B and *Halochlorella rubescens* BEA_IDA_0072B, and strains of cyanobacteria *Nodularia spumigena* BEA_IDA_0069B (according to a previous taxonomic study, the strain BEA_IDA_0069B had been identified with a species of *Anabaena* sp.) and *Nodularia harveyana* BEA_IDA_0070B (according to a previous taxonomic study, the strain BEA_IDA_0070B had been identified with a species of *Dolichospermum* sp.) exhibit efficient rates of biomass production and removal of contaminants when cultured in a culture medium prepared by diluting an effluent from a treatment plant in Gran Canaria in seawater at 0.5%, in such a way that, in the diluted effluent, concentrations of N—total nitrogen (ammonium and nitrate)—of 106 mg/l and concentrations of P—total phosphorus (orthophosphate)—of 3.75 mg/l are achieved. These concentrations result in an N/P quotient of 31.3.

Methods of the Invention

Thus, a first aspect of the invention relates to a method for producing biomass from a microalgae, wherein the method comprises culturing the microalgae in an effluent diluted in seawater, wherein the microalgae is selected from the group consisting of a strain of the genus *Nodularia,* a strain of the genus *Chrysoreinhardia,* a strain of the genus *Halochlorella,* and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range.

In a second aspect, the invention is related to a method for bioremediating an effluent, wherein the method comprises culturing a microalgae in the effluent diluted in seawater, wherein the microalgae is selected from the group consisting of a strain of the genus *Nodularia,* a strain of the genus *Chrysoreinhardia,* a strain of the genus *Halochlorella,* and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range.

In a general manner, biomass is understood as the material produced by the growth and/or propagation of cells, of microorganisms, plants or animals. The biomass can contain cells and/or intracellular content, as well as extracellular material. Extracellular material includes, but is not limited to, compounds secreted by a cell. In the context of the present invention, biomass is material produced by the growth and/or propagation of a microalgae.

According to the present invention, the term "microalgae" generally relates to a microorganism selected from eukaryotic microalgae and cyanobacteria. Eukaryotic microalgae are unicellular species that exist individually, or in chains or groups and that are typically found in freshwater and marine systems. Depending on the species, they can be anywhere from a few microns (μm) to a few hundred microns in size. Eukaryotic microalgae are capable of photosynthesis. They produce about half the atmospheric oxygen and simultaneously use the carbon dioxide from the greenhouse gas to grow photoautotrophically. Cyanobacteria are a group of photosynthetic bacteria, some of which fix nitrogen, that live in a wide variety of wet soils and water, either freely or in a symbiotic relationship with lichen-forming plants or fungi. They range from unicellular to filamentous and include colonial species. Colonies can form filaments, sheets or even hollow spheres.

In the methods of the present invention, the microalgae is selected from the group consisting of a strain of the genus *Nodularia,* a strain of the genus *Chrysoreinhardia,* a strain of the genus *Halochlorella,* and combinations thereof. In a previous taxonomic study, the strain of the genus *Nodularia* had been identified with a strain of the genus *Anabaena,* and/or with a strain of the genus *Dolichospermum. Nodularia* is a genus of cyanobacteria of the order Nostocales, of the family Aphanizomenonaceae. *Anabaena* is a genus of cyanobacteria of the order Nostocales, of the Nostocaceae family. *Dolichospermum* is a genus of cyanobacteria of the order Nostocales, of the family Aphanizomenonaceae. *Chrysoreinhardia* is a genus of the order Sarcinochrysidales and of the family Chrysocystaceae. *Halochlorella* is a genus of the Chlamydomonadales family. In a particular embodiment of the invention, the strain of the genus *Nodularia* is a strain of the species *Nodularia spumigena.* In a particular embodiment of the invention, the strain of the genus *Nodularia* is a strain of the species *Nodularia harveyana.* In a particular embodiment of the invention, the strain of the genus *Chrysoreinhardia* is a strain of the species *Chrysoreinhardia giraudii.* In a particular embodiment of the invention, the strain of the genus *Halochlorella* is a strain of the species *Halochlorella rubescens.* In a preferred embodiment, the strain of the species *Nodularia spumigena* is the strain BEA_IDA_0069B (according to a previous taxonomic study, the strain BEA_IDA_0069B had been identified with a species of *Anabaena* sp.). In a preferred embodiment, the strain of the species *Nodularia harveyana* is the strain BEA-IDA-0070B (according to a previous taxonomic study, the strain BEA_IDA_0070B had been identified with a species of *Dolichospermum* sp.). In a preferred embodiment, the strain of the species *Chrysoreinhardia giraudii* is the strain BEA-IDA-0071B. In a preferred embodiment, the strain of the species *Halochlorella rubescens* is the strain BEA-IDA-0072B. The strains were deposited on 25 Oct. 2019 at the Spanish Bank of Algae (University of Las Palmas de Gran Canaria, Muelle de Taliarte, s/n, 35214 Telde, Gran Canaria, Spain) according to the terms of the Budapest Treaty on the international recognition of the deposit of microorganisms for the purposes of the patent procedure with the deposit numbers BEA-IDA-0069B, BEA-IDA-0070B, BEA-IDA-0071B and BEA-IDA-0072B indicated respectively for each strain.

The terms "culturing a microalgae" or "microalgal culture" relate to a method or system for multiplying microalgae by means of reproduction in a predetermined culture medium, even under controlled laboratory conditions. The term "culture", and the variants thereof, relate to intentionally promoting growth (increase in cell size, cell content and/or cell activity) and/or the propagation (increase in the number of cells by mitosis) of one or more cells by using the planned culture conditions. The combination of growth and propagation can be called proliferation. The one or more cells can be those of a microorganism, like microalgae. Examples of planned conditions include using a defined medium (with known characteristics such as pH, ionic strength and carbon source), specified temperature, oxygen tension, carbon dioxide levels and growth in a bioreactor. Microalgal cultures can be used to multiply the organism, to determine the type of organism or the abundance of the organism in the sample being analysed. In liquid culture medium, the term "microalgal culture" generally relates to the entire liquid medium and to the microorganisms in the liquid medium, regardless of the container in which the culture resides. A liquid medium is often called a "medium" or "culture medium". The term "inoculate" relates to implanting or introducing microorganisms into a culture medium. Inoculating a microorganism culture under the culture conditions described throughout the specification relates to initiating a culture of microorganisms under the culture conditions, as commonly used in the art of microorganism cultures. Microorganisms that are introduced into a culture medium can be called a seed or an inoculum. In a particular embodiment of the present invention, the inoculation of the live microalgae in the culture medium is carried out, in terms of dry biomass, with at least 50 mg/l, preferably with 50-90 mg/l of dry biomass. In the present invention, microalgae can be cultured as a monoculture, or as co-culture. In an embodiment the culture is a monoculture. In another embodiment the culture is a co-culture of two, of three or of the four microalgae of the invention. The term "coculture" and the variants thereof relate to the presence of two or more types of cells (i.e., two or more types of microalgae) in the same bioreactor. The culture conditions can be those that promote the growth and/or propagation of the two or more types of cells or those that facilitate the growth and/or proliferation of one, or a subset, of the two or more cells while cell growth for the rest is maintained.

The term "effluent" or "leachate" in the context of the present invention relates to water discharges or runoffs used in industrial, urban or agricultural processes. Thus, the invention can be implemented with wastewater. Wastewater is any type of water the quality of which has been negatively affected by anthropogenic influence. Wastewater includes used, household, urban waters and the removed liquid industrial or mining waste, or the waters that were mixed with the foregoing (rain or natural waters). In a particular embodiment of the invention, the effluent or leachate comes from an anaerobic digester of a biomethanisation plant for the treatment of purification plant sludge, wherein the contaminant load exhibits approximately 4500 mg $N—NH_4^+/l$; approximately 550 mg $N—PO_4^{3-}/l$; approximately 150 mg $N—NO_3^-/l$ and approximately 40000 cfu/ml.

In the context of the present invention, the effluent is used diluted in seawater. In a particular embodiment, the dilution is of 50%, of 30%, of 20%, of 10%, of 5%, of 4%, of 3%, of 2%, of 1%, of 0.5%, of 0.4%, of 0.3%, of 0.2%, or of 0.1%. The diluted effluent exhibits, at the beginning of the culture, concentrations of total nitrogen (N) of 90±60 mg/l (i.e., in the 30-150 mg/l range), preferably in the 60-100 mg/l range and more preferably in the 70-90 mg/l range; concentrations of total phosphorus (P) of 8±7 mg/l (i.e., in the 1-15 mg/l range), preferably in the 2-10 mg/l range and more preferably in the 3-6 mg/l range. In the present invention, the N/P quotient is in the 5-40, 10-39, 15-38, 16-37, 20-36, 25-35 range. In a particular embodiment of the invention, the N/P quotient is preferably in the 15-38 range and more preferably in the 25-35 range. In a particular embodiment, the diluted effluent medium does not need the addition of an external amount of phosphorus (i.e., phosphate) to correct the N/P quotient. In an embodiment, the diluted effluent medium does not need any external additives.

In the context of the invention, total nitrogen (N) relates to the sum of the concentration of ammonium ($N—NH_4^+$) and the concentration of nitrates ($N—NO_3^-$) present in the diluted effluent, while total phosphorus relates to the concentration of orthophosphate ($N—PO_4^{3-}$) present in the diluted effluent. In the context of the invention, the N/P quotient relates to the ratio of the sum of the concentration of ammonium and nitrates present in the diluted effluent divided by the concentration of orthophosphate present in the diluted effluent. In a preferred embodiment, the unit of concentrations is expressed in mg/l. In a particular embodiment, the concentration of ammonium ($N—NH_4^+$) with respect to the concentration of total nitrogen (N) in the diluted effluent is of at least 50%, of at least 60%, of at least 70%, of at least 80%, of at least 90%, of at least 95%. In a particular embodiment, the concentration of ammonium (N-NR4±) with respect to the concentration of total nitrogen (N) in the diluted effluent is preferably of at least 60% and more preferably of at least 70%.

In the context of the present invention, the term "bioremediation" relates to a process used to treat contaminated media, in particular an effluent or wastewater, by altering environmental conditions in such a way that the growth of microorganisms is stimulated and the target contaminants are degraded. The present invention describes the use of microalgae as a biological system for the treatment of wastewater or effluent due to the ability thereof to remove significant amounts of nitrates, phosphates and organic matter. In many cases, bioremediation is less expensive and more sustainable than other remediation alternatives.

In a particular embodiment, the method further comprises the step of harvesting the biomass from the microalgae by filtration. In particular embodiments, the filtration is carried out through a 10 μm, 20 μm, 30 μm, 40 μm, 50 μm, 60 μm, 70 μm, 80 μm, 90 μm, or 100 μm mesh. In a preferred embodiment, the filtration is carried out through a 50 pm mesh. In a particular embodiment, the biomass harvested by the method of the invention is washed with an adequate solution, for example with distilled water or MilliQ water, and dried or lyophilised for later use.

For inocula of 50-90 mg/l of dry biomass, the methods of the invention achieve production yields of 5-200 mg/l d. In particular embodiments, the production yield is of at least 5 mg/l d, 10 mg/l d, 20 mg/l d, 30 mg/l d, 40 mg/l d, 50 mg/l d, 60 mg/l d, 70 mg/l d, 80 mg/l d, 90 mg/l d, 100 mg/l d, 110 mg/l d, 120 mg/l d, 130 mg/l d, 140 mg/l d, 150 mg/l d, 160 mg/l d, 170 mg/l d, 180 mg/l d, 190 mg/l d, 200 mg/l d. For inocula of 50-90 mg/l of dry biomass, the methods of the invention reach nutrient consumption rates of 4-30 mg/l d for total nitrogen (N) and 0.5-3.0 mg/l d for total phosphorus (P). In particular embodiments, the total nitrogen (N) consumption rate is of at least 4 mg/l d, 6 mg/l d, 8 mg/l d, 10 mg/l d, 12 mg/l d, 15 mg/l d, 20 mg/l d, 25 mg/l d, 30 mg/l d. In particular embodiments, the total phosphorus consumption rate is of at least 0.5 mg/l d, 0.6 mg/l d, 0.7 mg/l d, 0.8 mg/l d, 0.9 mg/l d, 1.0 mg/l d, 1.2 mg/l d, 1.4 mg/l d, 1.6 mg/l d, 1.8 mg/l d, 2.0 mg/l d, 2.2 mg/l d, 2.4 mg/l d, 2.6 mg/l d, 2.8 mg/l d, 3.0 mg/l d.

In a particular embodiment, the culture is carried out under outdoor environmental conditions. In a particular embodiment, the culture is carried out in photobioreactors. In particular embodiments, the photobioreactor is of at least 100 l, of at least 200 l, of at least 300 l, of at least 400 l, of at least 500 l, of at least 600 l, of at least 700 l, of at least 800 l, of at least 900 l, of at least 1000 l. In some embodiments, the bioreactor can be even larger, of 120000 l or more, for large-scale industrial applications. In a preferred embodiment, the culture is carried out in photobioreactors under outdoor environmental conditions, preferably in photobioreactors of at least 400 l.

In a particular embodiment, irradiation was from 0 μmoles photons/$m^2$·s (night-time) to 3000 μmoles photons/$m^2$·s (daytime), with an average of 1500 μmoles photons/$m^2$·s. In a particular embodiment, daytime irradiation can reach 3500 μmoles photons/$m^2$·s during peak light hours. Thus, in embodiments, the culture is carried out under a maximum irradiation of at least 1000 μmoles of photons/$m^2$s, of at least 1500 μmoles photons/$m^2$·s, of at least 2000 μmoles photons/$m^2$·s, of at least 2500 μmoles photons/$m^2$·s, of at least 3000 μmoles photons/$m^2$·s, of at least 3500 μmole photons/$m^2$·s. In embodiments, the culture is carried out under a mean irradiation of at least 1500 μmoles photons/$m^2$·s, of at least 1750 μmoles photons/$m^2$·s, of at least 2000 μmoles photons/$m^2$·s, of at least 2250 μmole photons/$m^2$·s. In a particular embodiment, the culture is carried out under a mean irradiation of at least 1750 μmoles photons/$m^2$·s.

In particular embodiments, the mode of operation of the bioreactor is discontinuous, semi-continuous or continuous. In discontinuous (batch) mode, the culture is carried out in lots or batches, without feeding (F); the total load of each culture or fermentation process (batch or lot) is placed inside the bioreactor and the production or fermentation process is allowed to take place for as long as necessary; which is referred to as the retention time. In semi-continuous mode (fed-batch), the culture is carried out by fed batches, with input feeding (F1); an input or feeding line (F1) is fed so that the culture system has a product (biomass) with maximum growth (exponential) and productivity increases. In continuous mode, the culture is carried out by chemostat, an input or feed line F1 is fed and an output line F2 or wash is drained; so that the flows or flow rates of both lines are equal and production is continuous. In a preferred embodiment, the mode of operation of the bioreactor is continuous culture.

The gas content of the bioreactor for culturing the microalgae of the invention can be manipulated. Part of the volume of the bioreactor may contain gas instead of liquid. Gas inlet ports can be used to pump gases into the bioreactor. Any gas can be pumped into a bioreactor, including air, $CO_2$, noble gases such as argon and others. The gas inlet rate into a bioreactor can also be manipulated. Increasing the gas flow in a bioreactor increases the turbidity of a microalgal culture. The gas inlet into a bioreactor can be modulated to generate optimal amounts of, for example $CO_2$, for maximum growth of the microalgae. Thus, in particular embodiments of the invention, the culture is carried out under a contribution of $CO_2$ by pulses of one minute every hour during daylight hours and/or aeration by means of a blower pump. In particular embodiments of the invention, the contribution of CO2 is 3% $CO_2$/97% air, 99.75% of air: 0.25% $CO_2$; 99.5% of air: 0.5% $CO_2$; 99.0% of air: 1.00% $CO_2$; 98.5% of air: 1.5% $CO_2$; 98.0% of air: 2.0% $CO_2$; 97.0% air: 3.0% $CO_2$, 96.0% air: 4.0% $CO_2$; and 95.00% air: 5.0% $CO_2$ can be infused into a bioreactor or bioreactor. In a particular embodiment, the culture is carried out under a contribution of $CO_2$ by pulses of one minute every hour during daylight hours (98.5% air: 1.5% $CO_2$) and/or aeration by means of a blower pump.

In a particular embodiment, the method according to the first aspect of the invention further comprises producing a processed material from microalgal biomass. Therefore, an aspect of the invention relates to a method for producing a processed material from microalgal biomass, wherein the method comprises: (a) producing microalgal biomass according to a method according to the first aspect of the invention, and (b) producing a processed material from microalgal biomass. The processed material is selected from the group consisting of a fertiliser, pesticide, feed, feed for fish, biofuel, jet fuel, biodiesel, pigment, surfactant, cosmetic, pharmaceutical agent, health supplement, or bioplastics. The processed material can be obtained by the appropriate steps to recover or extract the material from the microalgal biomass and to process the material.

Thus, an additional aspect of the invention relates to a method for producing a biomass extract of a microalgae, wherein the method comprises culturing the microalgae in an effluent diluted in seawater, wherein the microalgae is selected from the group consisting of a strain of the genus *Nodularia*, a strain of the genus *Chrysoreinhardia*, a strain of the genus *Halochlorella*, and combinations thereof, wherein the diluted effluent exhibits, at the beginning of the culture:

concentrations of total nitrogen (N) of 90±60 mg/l (i.e., in the 30-150 mg/l range), preferably in the 60-100 mg/l range and more preferably in the 70-90 mg/l range;

concentrations of total phosphorus (P) of 8±7 mg/l (i.e., in the 1-15 mg/l range), preferably in the 2-10 mg/l range and more preferably in the 3-6 mg/l range;

provided that the N/P quotient is in the 5-40 range, preferably in the 15-38 range and more preferably in the 25-35 range;

harvesting the biomass from the microalgae by filtration; subjecting the microalgal biomass to a cellular breakage method, and obtaining the extract resulting from cellular breakage.

Cellular breakage methods are generally known to those skilled in the art (see

E P247808961, or Jean-Maxime Roux, Hadrien Lamotte, Jean-Luc Achard, "An Overview of Microalgae Lipid Extraction in a Biorefinery Framework", Energy Procedia 112 (2017) 680-688). In a particular embodiment, the cellular breakage method is selected from the group consisting of ball mill, high-speed homogenisation, high-pressure homogenisation, ultrasonication, microwaves, pulsed electric field, chemical methods, enzymatic hydrolysis, and subcritical-water extraction.

All terms and embodiments described elsewhere in this document are equally applicable to these aspects of the invention, methods of the invention.

Macroalgal Biomass

A last aspect of the invention relates to a microalgal biomass obtainable by means of the method for producing biomass from a microalgae of the first aspect of the invention.

In embodiments of the present invention, the biomass content is 40-60% (dry weight, DW) of carbohydrates, 13-40% (dry weight, DW) of protein, and 2.7-20% (dry weight, DW) of lipids. In an embodiment, the protein content is 1%, 2%, 3%, 4%, 5%, 6%, 7%, 8%, 9%, 10%, 12%, 15%, 20%, 30%, 40%, 50%, 70%, 80%, 90%, or 100% greater in 0.5% effluent medium than in f/2 medium. In a particular embodiment, the protein content is 20% greater in 0.5% effluent medium than in f/2 medium for eukaryotic microalgae *Chrysoreinhardia giraudii* BEA_IDA_0071B. In a particular embodiment, the protein content is 26% greater in 0.5% effluent medium than in f/2 medium for eukaryotic microalgae *Halochlorella rubescens* BEA_IDA_0072B. In a particular embodiment, the protein content is 60% greater in 0.5% effluent medium than in f/2 medium for cyanobacterium *Nodularia spumigena* BEA_IDA_0069B (according to a previous taxonomic study, the strain BEA_IDA_0069B had been identified with a species of *Anabaena* sp.). In a particular embodiment, the protein content is 60% greater in 0.5% effluent medium than in f/2 medium for cyanobacterium *Nodularia harveyana* BEA_IDA_0070B (according to a previous taxonomic study, the strain BEA_IDA_0070B had been identified with a species of *Dolichospermum* sp.). In a particular embodiment, the protein content is, on average, 30%±20 greater in 0.5% effluent medium than in f/2 medium.

The biomass of a microalgae of the present invention complies with the European legislation for food products (Commission Regulation (EC) No. 2073/2005 of 15 Nov. 2005 on the microbiological criteria applicable to food products) or for maximum contaminant thresholds in food products (Commission Regulation (EC) No. 1881/2006 of 19 Dec. 2006, which establishes the maximum content of certain contaminants in food products), which determine that the number of aerobic microorganisms at 30° C. must be below 50,000 cfu/$g_B$ and that the presence of faecal coliforms must be undetectable in microbiology tests. The biomass of a microalgae of the present invention exhibits a heavy metal content that complies with the European standards on the maximum permissible content of heavy metals in seaweed and derived products (Commission Regulation (CE) No. 1881/2006 of 19 Dec. 2006, which sets the maximum content of certain contaminants in food products). These maximum concentrations are <3 mg/kg$_B$ for Pb and Zn, <0.3 mg/kg$_B$ for Hg.

In an aspect of the invention, the biomass of the invention can be used for the preparation of a pharmaceutical, nutraceutical, prebiotic, probiotic product or functional food. Particularly, the microalgae of the present invention are sources of PUFA (polyunsaturated fatty acids). In an additional aspect of the invention, the biomass of the invention can be used for the preparation of pesticides, feed, compound feed, fish feed and biofertilisers. In another aspect of the invention, the biomass of the invention can be used for the production of biodiesel, biofuel or jet fuel. Thus, the present invention further relates to the use of a microalgal biomass according to claim 16 to produce a processed material, wherein the processed material is selected from the group consisting of a fertiliser, pesticide, feed, feed for fish, biofuel, jet fuel, biodiesel, pigment, surfactant, cosmetic, pharmaceutical agent, nutraceutical product, prebiotic product, probiotic product, functional food, health supplement, or bioplastics.

All terms and embodiments described elsewhere in this document are equally applicable to this aspect of the invention, the biomass of the invention.

It should be noted that, as used in the specification and appended claims, the singular forms "a", "an", "the", include its plural referents unless the context clearly indicates otherwise. Similarly, the term "comprises" also includes as a particular embodiment that no additional elements or components are present, in other words, includes the term "consists of" as an embodiment.

EXAMPLES

The invention will be described by means of the following examples which are to be considered merely illustrative and not limiting of the scope of the invention.

1. Materials and Methods 1.1 Cultures of Strains and Media

The microalgal strains tested in this study are shown in Table 1. This table specifies where the strains were isolated, the type, class and morphology (filamentous or non-filamentous aggregate) thereof. The microalgae were obtained from the Spanish Bank of Algae (BEA for the acronym in Spanish) and belong to the group of species selected by the SABANA project (EU H2020, Grant #727874) with bioactive compound activity and significant productivity (see document "Deliverable 6.1, *Characterization of microalgae strains for agricultural and aquaculture applications at large scale*", https://cordis.europa.eu/project/id/727874/results). The inocula of the strains were cultured in semi-continuous mode (0.1 1/day) under the same laboratory conditions: light irradiation range between 220-280 μmol/m²·s (L:O 12:12), continuous supply of CO2 (1.5%), temperature (25±2° C.), pH (8.0±0.3) and f/2 marine medium (Guillard RRL, "Culture of Phytoplankton for Feeding Marine Invertebrates". In Smith W. L. and Chanley M. H. (Eds.), "Culture of Marine Invertebrate Animals", 1975 Plenum Press, New York, USA). The unit 1/day indicates that 10% of the volume is harvested and renewed (i.e., 50 ml, 250 ml, 1 1, 20 1, 400 1, etc.) per day.

1.2 Culture Conditions

The experiments were carried out outdoors in tubular packed bed reactors (PBR) of 400 1 volume for the strain BEA_IDA_0071B and 100 1 volume for the rest of the strains.

Units in triplicate were tested using f/2 medium as clean and control medium, and an additional set in triplicate using diluted effluent as a nutritional culture medium. These PBRs were inoculated with a different inoculum size (iPS) for each strain, ranging between 50 and 90 mg/l (PS, dry weight) (Table 5). The bubble PBR columns were kept outdoors without temperature and light control and constant aeration with pulse of CO₂ supply every hour (1.5%). The mean irradiance was 1750 μmol/m²·s and was measured every hour at different positions, using a spherical light sensor (LICOR, USA, SPQA 2770, LI-4000 mod.). The mean temperature, pH, salinity and conductivity range for each strain tested is shown in Table 2. These parameters were measured with previously calibrated CRISON Instruments (pH25 and CM25) portable sensors. The PBRs were operated in semi-continuous mode (with a dilution rate of 0.2 1/day) and replacing this volume daily with a new dilution of filtered seawater and medium (f/2 for controls and for the 0.5% effluent medium).

1.3 Culture Monitoring

20% of the volume of each PBR was harvested daily, using a 50 μm Nitex™ nylon mesh for filamentous and non-filamentous aggregate strains. The biomass was washed with doubly distilled sterile water, then frozen for 24 hours at −18° C. and subsequently lyophilised in a lyophiliser (Labconco, Freezone 6) for at least 48 hours and weighed to determine the biomass at steady state (g/l). The rejected water from the harvest was collected for the determination of the analysis (see below).

Production (P) was calculated as the daily biomass increase rate (g/l·d). The optical density (OD) of the cultures was calculated as the differences between the values verified at wavelengths of 680 and 750 nm in a Beckman Coulter DV 730 UV spectrophotometer against a reference seawater medium. The photosynthetic parameters were tested to determine the physiology of the strains in different media. A pulse width modulated chlorophyll fluorometer (AquaPen AP100, Photo-systems Instruments, Czech Republic) was used to control the physiological state of the cultures by measuring chlorophyll fluorescence as F0 and the Fv/Fm quotient as a measure of algal stress. An analysis of the chlorophyll a (Chl a) concentration was also carried out, by filtering 5 ml volume through GF/F fibre filters and subsequently extracting chlorophyll from the leachate in 90% acetone for 24 hours in the dark at 4° C. The fluorescence of the extract was measured on a Turner Designs Trilogy fluorometer complemented with a chlorophyll module without acidification (Turner Designs #7200-046) and previously calibrated with pure chlorophyll (Sigma Chem Co.) (Welschmeyer, N.A., 1994).

Chromophoric dissolved organic matter (CDOM) was measured by fluorescence in situ using a Turner Design fluorometer with an ultraviolet module (Turner Designs #7200-069) calibrated with a known concentration of quinine sulphate diluted in 0.05 molar $H_2SO_4$ at different levels, to determine the linear regression between fluorescence (RFU) and quinine concentrations (PPB). The removal of nutrients was calculated as the amount of nitrogen (ammonium and nitrate) and phosphorus eliminated by time and volume (mg Nutrient/l·d). The nutrient yield was calculated as the removal of nutrients by biomass production (mg Nutrient/$g_B$). The bacterial growth rate was calculated as the increase in the number of aerobic microorganisms (as a colony-forming unit, cfu) by volume and time (cfu/ml·d).

1.4 Analytical Methods 1.4.1 Water Analysis

A sample of the rejected water from the harvest and the volume of water replaced with the new nutrient medium was taken for different analyses. All procedures to analyse the composition of this water inlet and outlet from the PBR followed the standard analytical methods for water and wastewater from APHA (2017) and also from the Spanish Ministry of Agriculture (1982). The concentration of ammonium was determined by the Nessler method in which potassium, mercury and iodine react with ammonium to create a yellow-brownish compound proportional to the ammonium. The orthophosphate was measured photometrically through molybdenum blue reaction. The nitrates were determined by the cadmium reduction method. The bacterial concentration was measured by the horizontal method for enumeration of the colony of aerobic microorganisms counted at 30 degrees and 30° C. by the pour plate technique for food microbiology (ISO standard methods, 2018).

1.4.2 Effluent Analysis

Sequential thermometric titrations quantified carbonates and bicarbonates. Calcium, magnesium, potassium, sodium, boron, copper, iron, phosphorus, manganese and zinc were determined by inductively coupled plasma mass spectrophotometry (ICP-MS) and mercury by atomic spectrometry. The chemical oxygen demand (COD) was established by closed reflux photometry and the biochemical oxygen demand (5 days-BOD) by the manometric method.

1.4.3 Biomass Analysis

Once the biomass was lyophilised, biochemical, microbiological and heavy metals analyses were performed. The biochemical content of the biomass was studied with the analysis of carbohydrates, lipids, proteins and fatty acids. Carbohydrates were determined using the phenol-sulphuric method. The lipids were extracted with chloroform: methanol (2:1, v/v) with a BHT content of 0.01%. Once extracted, the lipids were dried and gravimetrically determined. Fatty acid methyl esters (FAME) were obtained from total lipids by means of acid-catalysed transesterification and identified by means of gas chromatography. The protein was quantified by the Kjeldahl method, consisting of digestion with sulphuric acid in the presence of a copper catalyst at 400° C., followed by distillation and assessment of the liberated ammonia. The protein value was obtained by multiplying the nitrogen (N) value×6.25. The microbiological analysis of the biomass was studied with the analysis of the presence of aerobic microorganisms at 30° C., *E. coli* β-D-glucuronidase, *Listeria monocytogenes,* faecal coliforms and *Salmonella* spp as cfu/g$_B$, following the ISO standard methods for Food Products, microbiology and feed (ISO standard methods, 2018). The biomass content of heavy metals (mercury, arsenic, cadmium and lead) was analysed for strain BEA_IDA_0071B as mg/kg$_B$ by atomic absorption spectrometry and plasma mass spectrometry (ICP-MS).

1.5 Statistical Analysis

All statistical analyses were performed with XLSTAT Addinsoft 2019.1 for Microsoft Excel. All experiments were performed in triplicate and variance studies (ANOVA) were carried out to determine the statistical significance of the variation in size observed between treatments. Levene's test was evaluated to evaluate homoscedasticity and the resulting p-values, and for results with significant difference (p value<0.05), the Kruskal Wallis test was carried out as a post-hoc analysis. To evaluate the differences between the mean values of the different parameters analysed for both analysed media (clean f/2 medium and effluent), Student's t-test was carried out with a 95% confidence level for normally distributed variables and Wilcoxon's paired pairs test for non-normally distributed variables. A Kolmogorov-Smirnov prior test was carried out to analyse the normal distribution. The null hypothesis established that the means are equal with a value of p>0.05. The principal components analysis (PCA) was carried out to analyse the Pearson correlation matrix between the main parameters analysed in f/2 medium and the different effluent dilutions analysed.

2. Results 2.1 Characterisation of the Effluent

The effluent used in these experiments is the rejected water from the anaerobically digested wastewater sludge from the biomethanisation plant of Salto del Negro (Gran Canaria, Canary Islands, Spain). This plant concentrates all the sludge material from the more than 40 treatment plants on the island of Gran Canaria (Government of the Canary Islands, 2019) for this anaerobic treatment. The composition range of this effluent (cations, anions, metals and other parameters) is shown in Table 3. The main compounds in this effluent were bicarbonates (17,531 mg/l), ammonium (4,200 mg/l), chloride (1,100 mg/l), potassium (604 mg/l), sodium (553 mg/l) and orthophosphate (525 mg/l). The amounts of metals (boron, copper, iron, manganese, mercury and zinc) were significant and also necessary for algal growth. In relation to the activity of microorganisms, Table 3 shows the BOD5 of the effluent, with mean values of 2,270 mg/l and COD values of 6,745 mg/l, which results in a BODS/COD quotient of 0.33, which indicates high amounts of biodegradable organic matter (related to a high CDOM value, 431 PPB) and highly contaminated water. This fact is also reflected in the high concentration of aerobic microorganisms at 30° C., 42,500 cfu/ml.

These results of the contaminated load of the effluent demonstrate the difficulty of finding an optimal dilution rate to use it as a nutrient medium to maximise the production of microalgae, same as f/2 marine medium. In this sense, the analysis of the main parameters of ammonium, phosphate, nitrate, N/P quotient, bacterial concentration, dry weight, CDOM and the physico-chemical parameters (salinity, pH and conductivity) was obtained for filtered seawater, for the f/2 medium, for the different dilutions of effluent in seawater (0.5%, 5%, 10%, 30% and 50%) and for the undiluted effluent (Table 4). All the above parameters (except CDOM, nitrate, bacterial concentration and N/P quotient) follow a similar pattern of linear proportionality for all percentages of effluent diluted in seawater ($R^2$>0.900, p>0.05). The table above shows the greatest similarity between the parameters analysed in a clean f/2 medium and 0.5% of diluted effluent ($R^2$>0.800, p>0.100) than in the rest of the effluent percentage dilutions ($R^2$<0.600, p<0.05). This closer link between the main parameters of the clean f/2 medium and 0.5% of the effluent can be verified by means of principal component analysis (PCA), wherein both nutrient media share the same quadrant (FIG. 1). The salinity of the undiluted effluent was 13‰ and that of the filtered seawater 38‰. While the salinity of the 0.5% diluted effluent was 36.8‰, similar to that of the f/2 medium. The conductivity of the diluted effluent (0.5%) was 57 mS/cm, which does not differ from the f/2 medium. The pH in medium diluted to 0.5% and f/2 medium ranged between 8.2 and 9, with a constant value of 7.9 for filtered seawater. The average amount of N (ammonium and nitrate) in the f/2 medium was 85 mg/l and 105 mg/l in 0.5% of diluted effluent. The orthophosphate in f/2 medium was 6 mg/l and 3.75 mg/l in 0.5% of effluent. The N/P quotient for these media was 14.7 for the control media and 31.3 for the diluted effluent. There was no bacterial activity in the filtered seawater, 518 cfu/ml in f/2 medium and 2.460 cfu/ml in 0.5% effluent. The CDOM in 0.5% of effluent was also greater than in the f/2 medium, 73.2 PPB and 30.4 PPB respectively (Table 4).

2.2 Outdoor Experiments

All experiments were carried out in triplicate in control medium (f/2) and 0.5% effluent at an exterior pilot scale in 100 l PBR for the strains BEA_IDA_0069B, BEA_IDA_0072B, BEA_IDA_0070B and in 400 l for the strain BEA_IDA_0071B. All the parameters studied (P, F0, Fv/Fm, OD, Chl a, BG, CDOM, removal of nutrients and yield) (Table 5) and (temperature, pH, salinity and conductivity) (Table 2) were validated for each medium with the analysis of variance (ANOVA) (for normally distributed variables) and Kruskal-Wallis (for non-normally distributed variables). No significant differences were shown for all variables and treatments (p>0.07) during the incubation period (15 days). The paired t-test did not show significant differences (p>0.05) between the previous parameters analysed in the f/2 and 0.5% effluent control medium (Table 2), Fv/Fm and CDOM ratio of the strain BEA_IDA_0071B, F0 and Chl a of the strain BEA_IDA_0070B (p<0.05) (Table 5).

Figure 2:
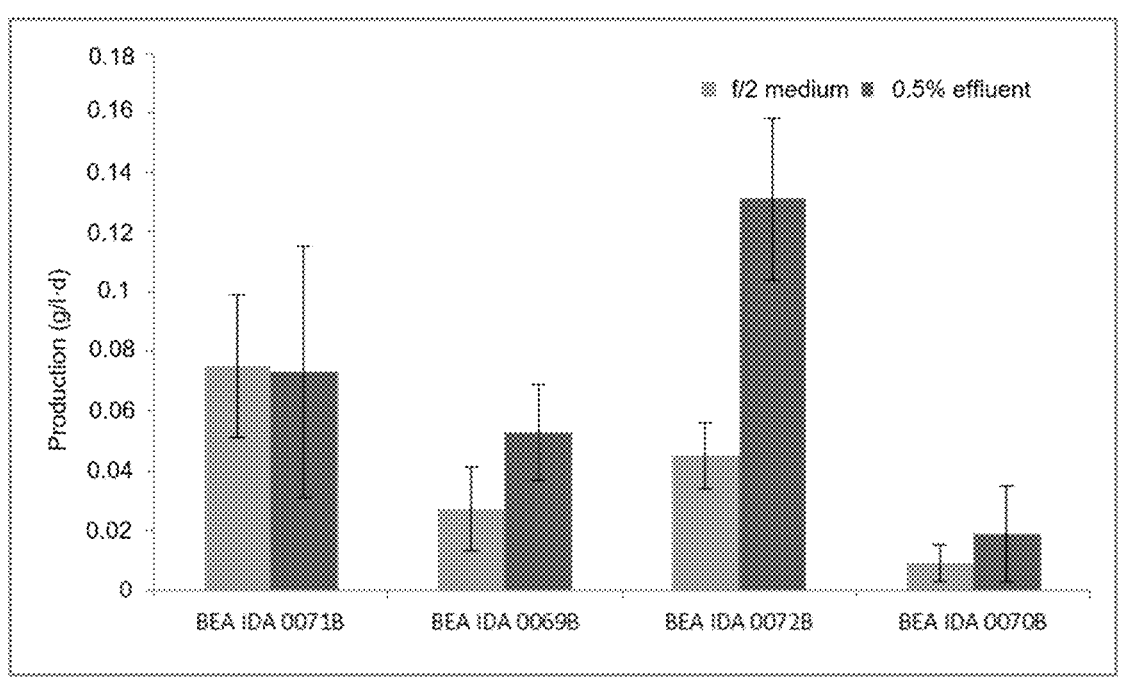
FIG. 2. Production (mean±SD) of the strains cultured in a clean f/2 medium and in 0.5% of effluent.

The production was greater in 0.5% of effluent than in f/2 medium for all the experiments carried out for all the strains, except for the microalgae BEA_IDA_0071B the production values of which were similar, 0.073 and 0.075 g/l·d (FIG. 2). The highest amount of production corresponded to the eukaryotic microalgae BEA_IDA_0072B in 0.5% of effluent (0.131 g/l·d), and BEA_IDA_0071B. It was observed how the lowest production values were related to the experiments carried out for the strains of cyanobacteria BEA_IDA_0069B and BEA_IDA_0070B, below 0.05 g/l·d in both media (Table 5). The paired production t-test analysis between f/2 medium and 0.5% effluent did not show significant differences (p>0.110).

The stress level of the microalgae during the entire incubation period was measured through the fluorescence Fv/Fm ratio. The lowest Fv/Fm ratio registered for the experiments carried out was for the microalgae BEA_IDA_0071B cultured in an f/2 medium, with a mean value of 0.530, which contrasts with the value of 0.610 in 0.5% of effluent (p<0.05). This mean value for the rest of the experiments carried out was approximately 0.700 and SD below 0.1 for both media (p>0.400) (Table 5). This maximum ratio value meant stress-free microalgal cultures. Fluorescence in vivo was measured as FO and showed a fairly significant positive linear correlation with the concentration of chlorophyll a (Chl a) (R=0.990). The lowest values (mean±SD) of fluorescence (F0 and Chl a) were registered for the eukaryotic strains BEA_IDA_0071B and BEA_IDA_0072B for both nutrient media carried out. The highest values corresponded to both strains of cyanobacteria. The optical density (OD) showed a higher level for 0.5% of the effluent experiments. This variable followed a similar procedural pattern to that of F0, with a significant Pearson correlation (R=0.855) (Table 5).

Figure 3:
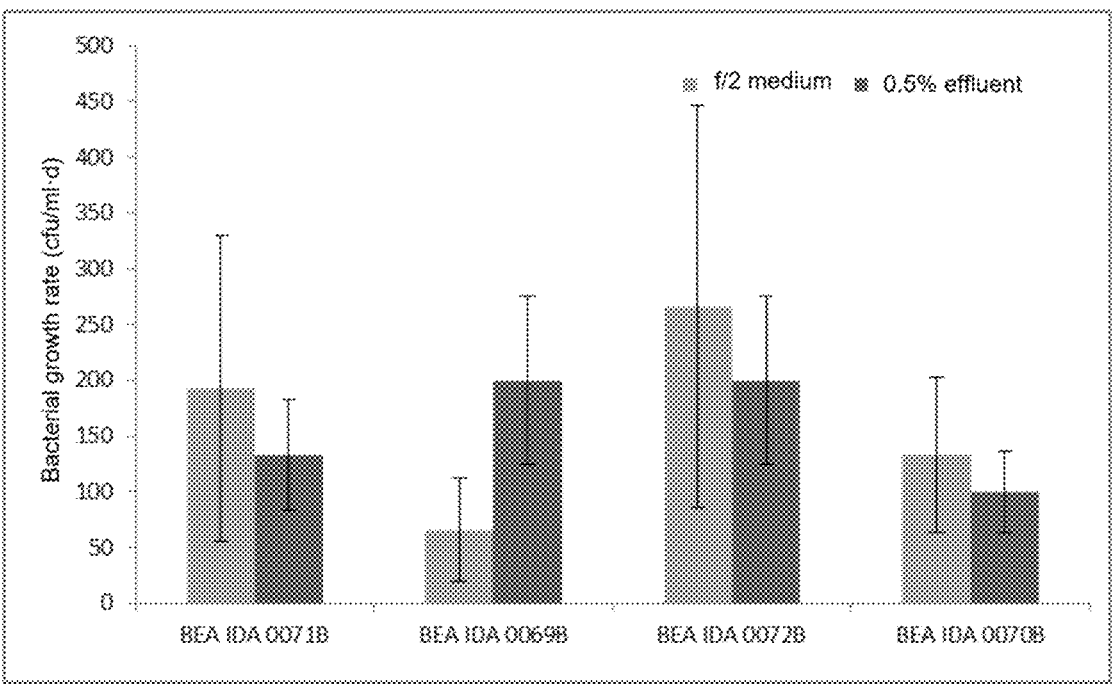
FIG. 3. Bacterial growth rate (cfu/ml·d) (mean±SD) for the different strains cultured in f/2 medium and in 0.5% effluent.

A growth of microorganisms was observed throughout the incubation period both in control medium (f/2) and in 0.5% effluent. It should also be taken into account that even bacterial growth was greater in f/2 medium cultures than in 0.5% effluent for strains BEA_IDA_0071B, BEA_IDA_0072B and BEA_IDA_0070B (FIG. 3). The lowest bacterial growth rate occurred in cyanobacteria BEA_IDA_0069B in clean medium (66 cfu/ml) and cyanobacteria BEA_IDA_0070B in 0.5% effluent (100 cfu/ml). The eukaryotic strain BEA_IDA_0072B showed the highest values of bacterial growth rate in f/2 medium (266 cfu/ml) and 0.5% effluent (200 cfu/ml). There were no significant differences between this parameter tested in both media (p>0.200). The expected CDOM was greater in 0.5% effluent than in f/2 medium (FIG. 4), with a mean value of 76 PPB for all strains except for cyanobacteria BEA_IDA_0070B, the value of which was 90 PPB. CDOM values in the control medium ranged from 19 to 46 PPB. There were no significant differences for the paired t-test analysis between the CDOM variable tested in both nutrient media (p>0.05), except for the microalgae BEA_IDA_0071B (p<0.05) (Table 5).

There were no significant differences between N removal, N yield, P removal and P yield for all the experiments carried out in clean medium and diluted effluent (p>0.08). It is worth noting the high mean value of N yield and N removal for the strain of microalgae BEA_IDA_0071B in both nutrient media: 78 $mg_N/g_B$ and 23.8 $mg_N/l \cdot d$ in f/2 medium, and 93 $mg_N/g_B$ and 24.9 $mg_N/l \cdot d$ in 0.5% effluent. For the rest of the strains, N yield varied between 20 and 55 $mg_N/g_B$ and N removal between 5 and 17 $mg_N/l \cdot d$ for both media carried out. P yield showed a narrower range of variation for all the strains and nutrient media used, between 2.3 and 5.4 $mg_P/g_B$, just like P removal, between 0.8 and 2 $mg_P/l \cdot d$ (Table 5).

2.3 Biomass Analysis 2.3.1 Microbiology

The microbiological analysis of the lyophilised biomass for all the microalgal strains analysed in the method and diluted showed that the study complied with the legislation in force for food products. This biomass exhibited values lower than the threshold established by legislation for the number of aerobic microorganisms at 30° C. (>50,000 cfu/gB) and faecal coliform bacteria (Absence) (Table 6).

2.3.2 Heavy Metals

The results of the main concentrations of heavy metals (Cd, Pb, Hg and As) in the biomass of microalgal strain BEA_IDA_0071B cultured in a clean medium and with 0.5% effluent, showed below the limits established in the current legislation for the control of heavy metals in algae and by-products (Table 7).

2.3.3 Biochemical Composition

There were no significant differences between the biochemical composition (carbohydrates, lipids, proteins and ashes) for all microalgal strains tested in a clean f/2 medium and 0.5% effluent, showing a significant determination rate (R2>0.900, p>0.05).

Figure 5:
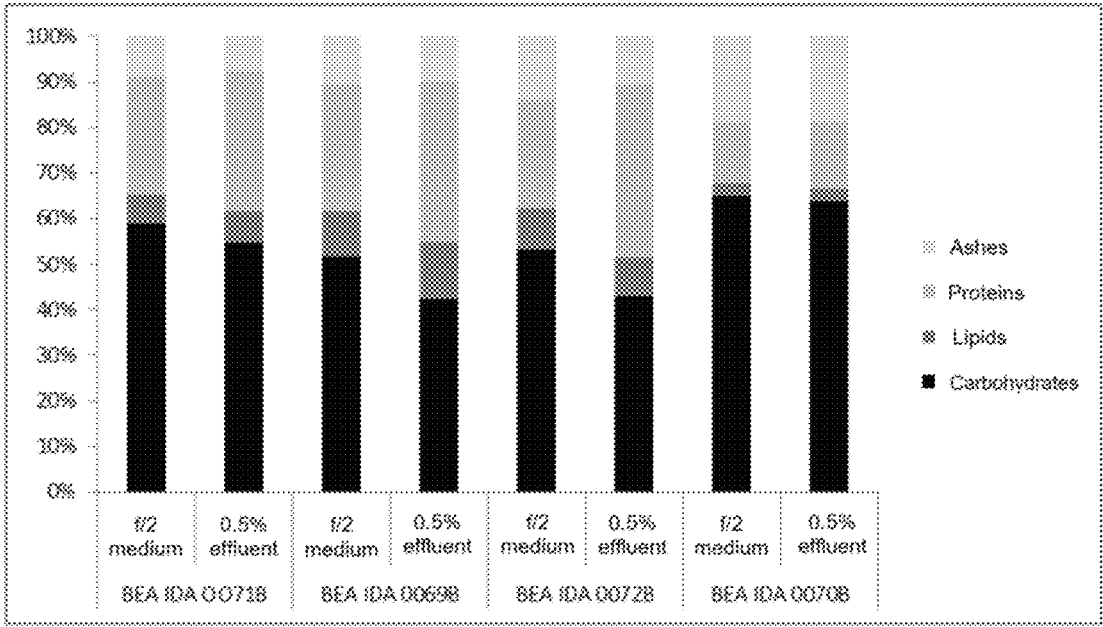
FIG. 5. Chemical composition of the microalgae strains tested in a clean f/2 medium and in 0.5% of effluent. The results are expressed as a percentage of the biomass in dry weight.

The carbohydrate content was slightly higher in the f/2 medium than in the diluted effluent and ranged between 40 and 65% (dry weight, DW). The strain of cyanobacteria BEA_IDA_0070B showed the greatest carbohydrate content both in the f/2 medium and in 0.5% of the effluent (>60% DW). For eukaryotic strains, the mean carbohydrate content was approximately 50% DW. The protein content ranged between 13 and 38% of DW, considerably higher in the effluent than in the f/2 medium for the strains BEA_IDA_0071B, BEA_IDA_0069B and BEA_IDA_0072B (with the highest values registered, 30-38% of DW, and similar for the strain BEA_IDA_0070B (with the lowest values registered, 13-24% (DW)). The lipid content was related between the two analysed media and ranged between 2.7 and 20.3% of DW. The cyanobacterium BEA_IDA_0070B showed the lowest values, <3% DW for both nutrient media. The ash content ranged between 7 and 14% of DW, except for the strain of cyanobacteria BEA_IDA_0070B, which showed values higher than 18% of DW (FIG. 5). There were also no significant differences between the fatty acid profile for all the strains tested in clean and effluent medium (p>0.800) (Table 8).

3. Discussion 3.1 Characterisation of the Effluent

The need for nutrients (nitrogen and phosphorus) for optimal growth results in microalgal culture comes at great cost. Today, the f/2 nutrient medium is expensive, but widely used in marine microalgal cultures. Therefore, the potential alternative use of wastewater as a source of nutrients for microalgal cultures appears to be a great challenge and is growing in strength, while working to reduce negative environmental impact. In this work, we have studied the use of diluted effluent as a source of nutrients for marine microalgae (cyanobacteria and eukaryotes). This effluent is the rejected water from anaerobically digested wastewater sludge from a biomethanisation plant in Gran Canaria (Canary Islands, Spain). The sludge from more than 40 treatment plants in Gran Canaria is treated in this facility. This mixture of wastewater sludge from urban, industrial and agricultural areas generates a high contamination load. This aspect is reflected in the composition range of the effluent, which shows high amounts of biodegradable organic matter, aerobic microorganisms (42,500 cfu/ml), DBO5 (2,270 mg/l) and DQO (6,700 mg/l). The concentrations of ammonium and phosphate were at relatively high concentrations (4,200 mg/l and 525 mg/l respectively), which are dangerous environmental contaminants with a very toxic potential (Table 3). These fairly high concentrations exceed the toxicity threshold for optimal algal growth. The composition of the effluent used in this study is ten times greater than that used in other research works in Spain. The dilution percentage of the effluent used in this work was 0.5%, well below the optimal 20% dilution used by previous authors. The nutritional compounds and the physico-chemical parameters of different percentages of effluent dilutions were correlated with the f/2 medium (Table 4, FIG. 1) as shown in the results. Therefore, we consider the 0.5% effluent as a starting point to consolidate the effluent as a nutrient medium for microalgal production and compare/evaluate it with the consolidated f/2 medium. In light of the results, it was shown that the concentration of aerobic bacteria grew exponentially along the percentage of effluent dilution (R2=0.980, p>0.05), producing degradation of the nitrogen present in the effluent. This fact implied a significant degradation of ammonia through dilutions in seawater, due to the ammonification process. When dilutions were carried out in the effluent, the aerobic bacteria present in the effluent (anaerobic environment) found a favourable environment for optimal growth, by breaking down organic nitrogen into ammonia, that in this seawater medium becomes ammonium. This organic nitrogen from the effluent, under anaerobic conditions, remains stable but diluted in seawater precipitates as ammonium due to bacterial activity. This ammonium under aerobic conditions stimulates the oxidation of ammonium into nitrates (nitrification process through the action of Nitrosomonas and Nitrobacter bacteria). The results of ammonium and phosphate showed a linear proportionality pattern through the different dilutions of effluent ($R^2 > 0.900$, $p > 0.05$), but a logarithmic pattern on the concentration of nitrate ($R^2 > 0.890$, $p < 0.05$), due to this nitrification process. This fact is fundamental, the concentrations of inorganic nitrogen (nitrate and ammonium) in the effluent with respect to the concentrations of phosphate produced an N/P quotient of 31.3 for a dilution of 0.5% of the effluent, an N/P quotient of $11.1 \pm 2.3$ for a dilution of 5% and a quotient of approximately 6 for effluent dilutions between 10 and 50% (Table 4).

In this sense, the CDOM showed, as explained in the results, that there is no significant difference with the bacterial and nitrate concentration ($p > 0.05$). Dissolved organic matter is an important determinant of the underwater light field in natural waters. The CDOM absorbs light in both the ultraviolet and visible wavelengths, reducing radiation for photosynthesis. The organic matter produced and released by phytoplankton during growth is produced by heterotrophic bacterial communities that transform dissolved organic matter into biomass and recycle inorganic nutrients. This fact could explain the direct relationship between CDOM and the microbial concentration in the range of effluent dilution (Table 4), in the formation of CDOM by bacterial transformation. As with a bacterial concentration that increases significantly through the effluent percentage, CDOM showed a linear evolution, closely related to that concentration percentage ($R^2 > 0.780$, $p > 0.05$). This relationship suggests that the effluent diluted in seawater increased microbial activity, which led to further degradation of the organic matter in the effluent. This aspect is reflected as a significant increase in CDOM, dissolved organic matter that serves as a substrate for the heterotrophic microbial remineralisation of other elements. Microbes use extracellular enzymes to catalyse a high molecular weight of organic matter into smaller compounds that can be transported across bacterial cell membranes. There is an important link between CDOM fluorescence production and the microbial processing of organic matter.

It was observed that this effluent dilution of 0.5% maintained nitrogen and phosphorus levels in an acceptable proportion for algal growth (N/P quotient of 31.3), higher than this proportion obtained by other authors in the entire range of effluent dilution percentages (13.5). This dilution of 0.5% of effluent chosen to carry out the production experiments showed an acceptable level of total phosphorus (3.75 mg/l) and total nitrogen (106 mg/l), without the need to add an additional amount of P to correct the N/P quotient, as was done in other works with effluent (Sepúlveda, C., Acién, F. G., Gómez, C., Jiménez-Ruiz, N., Riquelme, C., Molina-Grima, E., 2015. *Utilization of centrate for the production of the marine microalgae Nannochloropsis gaditana.* Algal Res. 9: 107-116; Romero-Villegas, G. I., Fiamengo, M., Acién-Fernández, F. G., Molina-Grima, E., 2018. *Utilization of centrate for the outdoor production of marine microalgae at pilot-scale in flat-panel photobioreactors.* Journal of Biotechnology 284: 102-114).

From this dilution, the concentration of ammonium increased significantly throughout the effluent dilution percentage, reaching toxic levels (Table 4). The concentration of ammonium for the 0.5% of effluent was 72 mg/l and far exceeded the toxicity limit values of 1.8 mg/l for more than 200 species of marine phytoplankton, 16.22 mg/l for *Nannochloropsis* sp, 9 mg/l for *Spirodela polyrrhiza*, 27 mg/l for *Uroglenopsis americana, Synura petersenii* and *Dinobryon cylindricum*, 3.14 mg/l for *Nephroselmis piriformes*. Previous studies on the effect of high concentrations of ammonium on the optimal growth of the different classes of microalgae have established threshold values at 137 mg/l for Chlorophyceae, 45 mg/l for Cyanophyceae, 25 mg/l for Prymnesiophyceae, 6 mg/l for Diatomophyceae, 4.6 mg/l for Oxyrridea and 1.8 mg/l for Dynoplyceae. In the same review, the toxic level for Chlorophyceae was established at 703 mg/l and 234 mg/l for Cyanophyceae. In this sense, other works with *Chlorella vulgaris* established an ammonium toxicity level of 360 mg/l. All these previous references showed that the toxic ammonium limit for the effluent used was available up to 5% of the dilution of the effluent, taking into account that the strains analysed in this work belong to the class of the Cyanophyceae (BEA_IDA_0069B and BEA_IDA_0070B), the Chlorophyceae (BEA_IDA_0072B) and the Pelagophyceae (BEA_IDA_0071B). The concentration of ammonium can substantially increase to toxic levels when the pH exceeds the value of 9, producing an inhibition in algal growth. In this work, the pH remained constant and below this value during the culture period (Table 2).

3.2 Outdoor Experiments

The production results showed the best results for the operations carried out in a medium with effluent diluted to 0.5% than in a clean f/2 medium for all the strains analysed (FIG. 2, Table 5). The highest values corresponded to the eukaryotic strains BEA_IDA_0072B (131 mg/l·d) and BEA_IDA_0071B (73 mg/l·d). It is observed that these production rates are relatively low in relation to those obtained by other authors in media with diluted effluents: 320 mg/l·d for *Nannochloropsis gaditana*, 1130 mg/l·d for *Muriellopsis* sp and 1020 mg/l·d for *Pseudokirchneriella subcapitata*, 920 mg/l·d for *Chlorella* sp, 900 mg/l·d for *Scenedesmus* sp, *Auxenochlorella protothecoides* in wastewater, 200 mg/l·d for *Chlorella sorokiniana*, but higher than those reported by other authors. Differences in production arise according to the strain, the culture medium, the established operating conditions, the dry weight inoculum, the type of wastewater or effluent and the dilution rate. For this study, we have operated within a dilution rate of 0.2 1/day when other authors found the best productivity between 0.3 1/day and 0.6 1/day. Given the best results obtained in productivity by the previous authors, we could increase the dilution rate to 0.6 1/day to improve the yield of our production experiments.

The Fv/Fm ratio was measured in all the experiments carried out, showing a mean value of 0.680 and a low SD (0.05) for all strains and media studied. This proportion was estimated to control the stress level of the cultures and showed healthy and stress-free cultures that were perfectly suitable for the established outdoor conditions and the nutrient media. Low values of the Fv/Fm ratio would be expected due to the physico-chemical conditions of the culture in outdoor conditions and in an effluent medium. However, the difference (Fv) between the maximum (Fm) and minimum (F0) fluorescence showed higher values related to these significantly high Fv/Fm ratios. The greater the stress of the microalgae, the fewer open reaction centres available and Fv/Fm. An Fv/Fm ratio close to 0.800 can be considered optimal in physiological terms, showing an increase in active PSII (photosystem II) reaction centres, which indicates a stress-free situation. It is accepted that these values physiologically acclimatise to environmental conditions. The Fv/Fm ratio has been related to the maximum quantum yield of PSII photochemistry and a decrease in this ratio reflects damage to PSII, symptomatic of an unbalanced accumulation of reducing power, which in turn promotes the synthesis of lipids. That means that a drastic decrease in normal cell function induced the formation and accumulation of intracellular lipids. Changes in Fv/Fm provide essential information on the effects of microalgal physiology due to nutrients, stationary phase, density, collection, pH. For all these reasons, we can ensure that our experiments were carried out under optimal conditions for the incubation period in both tested nutrient media.

It is also important to study bacterial growth in microalgal production using effluent or wastewater as a source of nutrients, since the bacterial loads in the effluent could be considerable (in this case, 42,500 cfu/ml). It is also relevant to contrast the results with those obtained with a clean or control medium, in our case f/2 medium. Our results have shown that there is no significant difference between the bacterial growth rate analysed in experiments carried out in a clean medium and 0.5% of diluted effluent (p>0.200, Table 5). The mean differences between the bacterial growth rates measured in both nutrient media for all the microalgae analysed were only 60±15 cfu/ml. Therefore, we may not consider microbial growth in these cultures with 0.5% effluent as a limiting factor, which also shows a positive relationship with algal production (R=0.700, p<0.05). However, it is reasonable to expect interactions between algae and bacteria from the wastewater, some authors found that 50% of the total nitrogen in such cultures could be assimilated by microorganisms. It would be a mistake to consider that all the nutrients removed in these cultures with wastewater or effluent as a nutrient medium are exclusively due to algal growth. It is evident that the Nitrosomonas bacterium dissolves a process of transformation of ammonium dissolved in water to nitrite, right after the Nitrobacter bacterium oxidises nitrite turning it into nitrate. It is also important to note that, under the ammonification process, decomposing organic matter turns into gaseous ammonia and then into ammonium. There are not many studies characterising this microbial consortium in wastewater or effluent culturing. Bacteria associated with effluents can interact directly or indirectly with the microalgal strain through commensalism, mutualism and parasitism.

Little is known about the interactions, and this fact could limit our ability to develop a coherent hypothesis to be tested in such cultures. There are more questions than answers on bacterial algal interactions and it has not been exploited in algal-based technologies. More research is needed to find the optimal conditions for the simultaneous removal of ammonia and nitrate from microalgae and bacteria.

Microalgae can assimilate nitrogen from a variety of sources such as ammonium, nitrate and urea, preferring to assimilate ammonium to glutamine and release the hydrogen ion. This assimilation does not require the redox reaction and uses less energy than other sources of inorganic nitrogen. In the experiments carried out in this work, nitrogen and phosphorus were efficiently removed for all microalgae analysed. No significant differences were observed between the removals of nutrients analysed in the control f/2 medium and the 0.5% effluent medium (p>0.05). N removal showed the lowest values for the strains of cyanobacteria, 5.8 $mg_N$/l·d for BEA_IDA_0070B and 10.1 $mg_N$/l·d for BEA_IDA_0069B for clean f/2 medium and 6.9 $mg_N$/l·d and 11.2 $mg_N$/l·d for 0.5% effluent (Table 5). These results are higher than 4 $mg_N$/l·d, obtained for *Anabaena* sp in built wetlands, or 3.5 $mg_N$/l·d for *Phormidium bohneri* in water treatment. N removal for the eukaryotic strains showed similar or higher values for these strains cultured in the effluent medium than in the algae medium, with values between 12 and 25 $mg_N$/l·d. This range of values was also in line with those obtained for *Scenedesmus* sp. in effluent at a dilution rate of 0.2-0.6 1/day, *Pseudokirchneriella subcapitata* in effluent, *Nannochloropsis gaditana* at 0.3 1/day dilution rate, *Chlorella* sp. in effluent and in pig slurry for some microalgal cultures. Our N removal results appear to be greater than those obtained in wastewater for *Scenedesmus* sp. (8.8 $mg_N$/l·d), but lower than those obtained in the effluent for: *Muriellopsis* sp (47.5 $mg_N$/l·D), *Nannochloropsis gaditana* at a dilution rate of 0.2 1/day. P removal in the experiments carried out in this work ranged between 0.8-2 $mg_P$/l·d without significant differences between the two nutrient media tested (p>0.05). These results were in agreement with those obtained in a microbial consortium medium with *Chlorella vulgaris* (0.576 $mg_P$/l·d, in wastewater with *Pseudokirchneriella subcapitata* and *Scenedesmus* sp. It was observed that these values were lower than those obtained in effluent with *Scenedesmus* sp, *Nannochloropsis gaditana*, with *Murelliopsis* sp and for freshwater algae cultured in wastewater. There were no significant differences between the N yield values between the experiments carried out in both nutrient media (p>0.05) with a range value between 20.1-93 $mg_N$/$g_B$. The highest value corresponded to the eukaryotic strain BEA_IDA_0071B (Table 5). These data were in line with those obtained in effluent with *Scenedesmus* sp (23.3-37.6 $mg_N$/$g_B$), *Nannochloropsis gaditana* (50 $mg_N$/$g_B$), *Murelliopsis* sp (50 $mg_N$/$g_B$), *Chlorella vulgaris* (51 $mg_N$/$g_B$) and for filamentous green algae in wastewater treatment. In relation to our P yield results, there were no significant differences either between the nutrient media used (p>0.05) with a range value between 2.2 and 5.4 $mg_P$/$g_B$, with the highest value corresponding to the cultured cyanobacteria BEA_IDA_0069B in clean medium. These results were similar to those obtained in effluents at the same dilution rate for *Scenedesmus* sp, at a dilution rate of 0.3 1/day for *Nannochloropsis gaditana* and in wastewater for *Murelliopsis* sp and higher than *Murelliopsis* sp in effluent (3.2 $mg_P$/$g_B$).

These results obtained are in line with others obtained in different research works as shown above. Once again, these results show the effectiveness of the use of microalgae to remove nutrients from effluents and wastewater. We also highlight the N yield of the eukaryotic strain BEA_IDA_0071B in an effluent with a value of 93 $mg_N$/$g_B$. This value was much greater than those obtained by other effluent research works in the use of effluent or wastewater as a nutrient medium for the production of microalgae.

Figure 4:
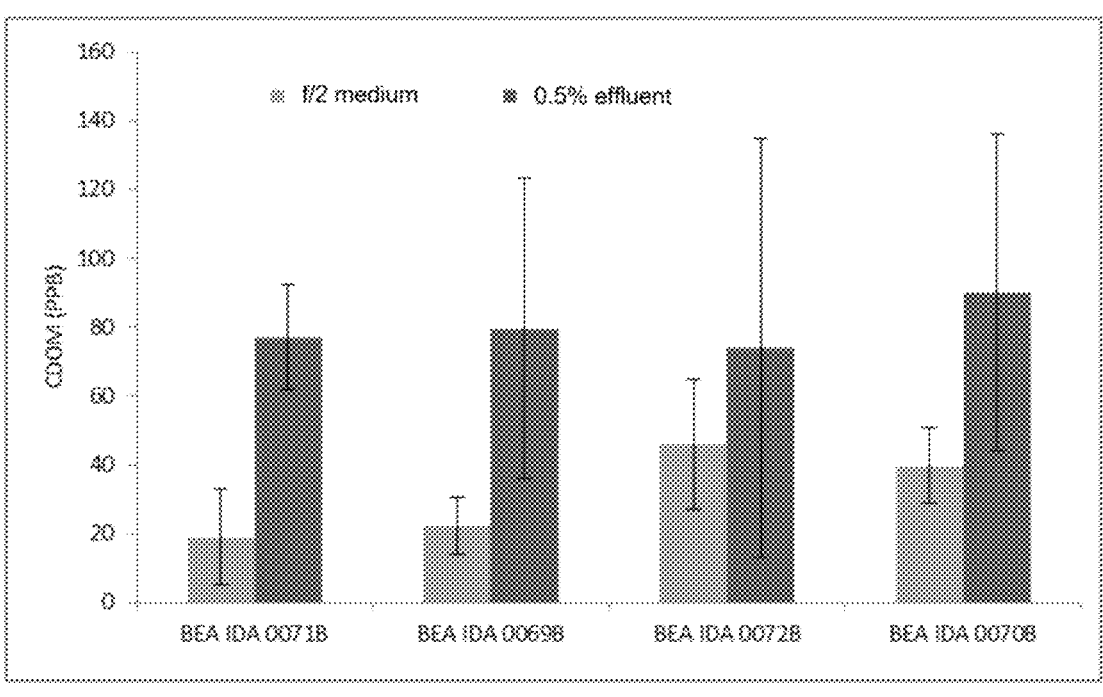
FIG. 4. CDOM (PPB) (mean±SD) for the different strains cultured in f/2 medium and in 0.5% of effluent.

It is observed in our results that the average CDOM in the cultures carried out in diluted effluent was at least two times greater than in the control f/2 medium (FIG. 4). This fact confirms a greater microbiological activity in 0.5% of the effluent, due to the role in the formation of CDOM by bacterial transformation. Unfortunately, this is a critical aspect and has not been widely studied.

3.3 Harvest

The cost to harvest microalgal biomass could be a barrier to its potential applications. Centrifugation methods are energy intensive and flocculation is also expensive and could increase the salinity of the harvested biomass. On this matter, all the strains tested in this work were collected by filtering biomass through a 50 μm mesh. The strains of cyanobacteria BEA_IDA_0069B and BEA_IDA_0070B were filamentous and tend to form aggregates, the eukaryotes BEA_IDA_0071B and BEA_IDA_0072B form aggregates and all of these strains tend to sink and form a thin layer of sediment when aeration was discontinued. All this enables the biomass to be collected in an efficient, fast and comfortable manner. Before proceeding with the lyophilisation of the biomass, it can be washed thoroughly with distilled water. This form of collection enables the dissolved solid matter, bacteria and toxic compounds to be removed from the biomass as well as impurities to be greatly reduced. This fact represents a total advantage over most of the microalgae cultured in other studies, wherein the microalgae exhibit a small cell morphology below 5 μm in diameter, they do not sink and do not form aggregates. Due to these features, these microalgae in other studies must be harvested by centrifugation. This methodology and morphology of the microalgae in other studies do not enable the biomass to be washed.

3.4 Biomass 3.4.1 Microbiology

This study is the result of the microbiology results of the lyophilised biomass analysed for the experiments carried out in a clean f/2 medium and diluted effluent. All the biomass of the strains collected through the mesh showed compliance of the analysis with current European legislation for food products (EC regulation, 2005) and with the maximum contamination threshold in food (EC regulation, 2006) (Table 6). These results confirm the viability, potential and benefits of these strains that exhibit the advantage of being harvested by mesh, as described in the previous section. However, the water rejected from the process has concentrations of ammonium, nitrate and phosphate, dissolved organic matter and microorganisms below the threshold of the admissible values established in the Spanish regulations for the reuse of treated water (Ministry of the Presidency of Spain, 2007) as explained in the results and reflected in the respective previous sections. The water bioremediation process of leachate using microalgae for nutrient removal is highly effective.

3.4.2 Heavy Metals

The heavy metal content of the harvested biomass for the microalgae strain BEA_IDA_0071B meets the criteria of European recommendations on the limit content of heavy metals in seaweed and by-products (EC Regulation, 2006). This maximum concentration was established at <3 mg/kg$_B$ for Pb and Zn, <0.3 mg/kg$_B$ for mercury. The effluent showed concentrations of mercury of 0.075 mg/l, and was diluted in seawater at 5%. This concentration decreased to 0.075 μg/l. This concentration could be considered not significant. Therefore, the concentration of mercury in the biomass analysed for both nutrient media tested showed to be below the threshold value, <0.09 mg/kg$_B$ (Table 7). In this aspect, it has been taken into account that the biomass of this strain could be washed since it was possible to harvest it through the mesh.

3.4.3 Biochemical Composition

The results revealed that carbohydrates were the dominant biomass fraction for all strains and that both nutrient media were in the value range obtained for the microalgal biomass cultured in PBR (>43% DW) (FIG. 5). The carbohydrate values of the green microalgae BEA_IDA_0072B were in line with those obtained for Chlorella sp, Scenedesmus sp in effluent at a dilution rate of 0.2 1/day and Nannochloropsis gaditana in effluent medium at a dilution rate of 0.3 1/day described by other authors. This value was slightly greater in the golden algae strain BEA_IDA_0071B (50% DW) than in the golden microalgae Prymnesium parvum (40% DW). The carbohydrate content of the cyanobacteria BEA_IDA_0070B and BEA_IDA_0069B was more significant (>40% DW) than the values registered in other studies for Anabaena cylindrica (30% DW), but similar to those values registered by other authors in Spirogyra sp. The concentration of lipids in most species is between 2 and 19% DW (FIG. 5). These distance values were obtained in Nannochloropsis gaditana in effluent medium by other authors, but lower than those reported in Scendesmus obliquus in pig wastewater (31% DW). The Fv/Fm ratio during the incubation period carried out for all strains and nutrient media (Table 5) did not induce the accumulation of lipid content as it occurred under stressful conditions. It should be taken into account that the differences in concentrations of lipids are a function of different factors (medium and concentration of nutrients, dilution rate, outdoor conditions). Our results showed that proteins were the other main compounds with concentrations varying between 13 and 40% DW, with higher values for the biomass cultured in 5% of effluent. This benefit range was similar for various microalgal strains cultured in PBR by other authors with values >45% DW for Chlorella sp and Tetraselmis chuii and that obtained for Nannochloropsis gaditana, Chlorella vulgaris and Chlorella sp, but higher than those of Scenedesmus sp cultured in effluent medium. The microalgae Prymnesium parvum showed a protein content similar to the strain BEA_IDA_0071B tested in both nutrient media in this work.

The ash content range registered (7-20% DW) (FIG. 5) is consistent for marine microalgae with low ash content (<10% DW) for the eukaryotic microalgae BEA_IDA_0071B and moderate ash levels (10-20% DW) for the microalgal strain BEA_IDA_0072B. This range value is related to the greater ash content registered for different green and golden microalgae, as well as for cyanobacteria. The microalgal strains tested in this work showed a different biochemical composition, with a predominance of carbohydrate content, followed by proteins and, to a lesser degree, by lipids and ashes. The best source of carbohydrate content seemed to be in microalgae cultured in a clean medium, and on the contrary, microalgae cultured in diluted effluent showed a high protein content. The lipid content is transparent to the nutrient media used. Table 8 shows the fatty acid profile data. Currently, their interest is mainly in the production of PFA, such as eicosapentaenoic acid (EPA, 20:5) and docosahexaenoic acid (DHA, 22:6). In this sense, the strain BEA_IDA_0071B showed the highest EPA values (20:5) and more significant than those obtained by other authors for microalgae of the Pelagophyceae class, Chlorophyceae and Tetrasemis sp. class. The DHA content (22:6) was greater in the cyanobacterial strains and the eukaryotic BEA_IDA_0072B. These values appeared to be higher in the effluent medium than in the control medium, and also higher than those obtained for cyanobacterial strains by other authors. Alpha-linolenic acid (ALA, 18:3) showed the lowest values for the microalgae BEA_IDA_0071B, ranging between 13% and 19.3% for the rest of the strains analysed. These data were higher than those obtained by other authors (<13%) for Scenedesmus sp cultured semi-continuously in untreated wastewater at different dilution rates, but lower than those obtained for the same species by other authors (39.3%). Oleic acid (18:1) was greater for the microalgal strain BEA_IDA_0072B, with a range between 25% and 29%, showing higher values than for Chlorella sp and for Scenedesmus sp. The palmitic acid data (16:0) showed a value similar to that obtained for different species and microalgal studies.

All strains tested showed a PUFA % to SFA % ratio greater than 1, except for cyanobacteria BEA_IDA_0070B in f/2 medium. In addition, in cyanobacterial strains and microalgae BEA_IDA_0072B, most of these PUFAs are n-3 PUFAs, with an n-3/n-6 ratio greater than 1. These strains showed good sources with DHA levels between 1% and 2% (Table 8). These results are far from the adequate DHA levels reported by other authors for *Rhodomonas* sp (4.6%) and *Isochrysis galbana* (12.7%).

The previous results address the potential of the microalgae tested in this work as sources of PUFA and can be applied as sources of functional foods, nutraceuticals and pharmaceuticals. The relatively high content of SFA % and MUFA % (>60%) for all strains except microalgae BEA_IDA_0071B (<40%) offers the possibility of achieving the production of biodiesel with superior oxidative stability.

4. Conclusions

The use of 0.5% effluent diluted in seawater can achieve significant production rates at a dilution rate of 0.2 1/day, and production could be improved by increasing this dilution rate to 0.6 1/day. This aspect must be studied in considerable depth.

The strain BEA_IDA_0071B showed the maximum N removal (24.9 mgN/l·d) and N yield (93 mgN/g$_B$). P removal varied between 0.8 and 1.2 mgP/l·d and P yield varied between 2.2 and 4.8 mgP/g$_B$. The experiments carried out did not show significant differences in bacterial growth in both nutrient media throughout the incubation period, despite the greater microbiological activity in the effluent medium as shown in the CDOM results.

The microbiological analysis of the biomass confirms the viability, potential and benefits of the strains harvested through a mesh and washed with distilled water because these results showed compliance with current legislation for food products. Biochemical analysis showed that carbohydrates were the dominant fraction 40-60% DW, followed by proteins 13-40% DW, then lipids 2.7-20% DW for all strains and nutrient media. BEA_IDA_0070B showed the maximum carbohydrate content (64% DW), BEA_IDA_0072B the maximum protein content (38% DW). Following the above, each one of the marine strains studied in this work offers enormous potential for wastewater treatment, easy collection, bacterial growth control and clean biomass with a wide range of possibilities (pesticides, aquaculture feed, compound feed, biofertilisers, biodiesel, nutraceuticals and pharmaceuticals).

The use of effluent as an alternative source of nutrients for microalgal cultures appears to be attractive while reducing the serious and dangerous problem of environmental impact due to treatment and discharges. These preliminary results support the possibility of producing valuable microalgal biomass that purifies wastewater or effluent, prevents bacterial growth and provides a water supply.

TABLE 1

Microalgal strains used for the production of biomass in effluent.

| Code | Strain | Isolated | Type | Morphology | Class |
|------|--------|----------|------|------------|-------|
| BEA_IDA_0069B | *Nodularis spumigena* | Hypersaline | Cyanobacterium | Filamentous | Cyanobacterium |
| BEA_IDA_0070B | *Nodularis harveyana* | Seawater | Cyanobacterium | Filamentous | Cyanobacterium |
| BEA_IDA_0071B | *Chrysoreinhardia giraudii* | Seawater | Eukaryote | Non-filamentous aggregate | Pelagophyceae |
| BEA_IDA_0072BB | *Halochlorellarubescens* | Seawater | Eukaryote | Non-filamentous aggregate | Chlorophyceae |

TABLE 2

Results (Mean ± SD) of the main physico-chemical parameters (conductivity (mS/cm), temperature (° C.), pH and salinity ‰)) measured in f/2 medium and 0.5% of effluent medium for each of the microalgal strains tested. Bold means that there is a significant difference between the nutrient media ($p < 0.05$).

| | Strain | mS/cm | ° C. | pH | ‰ |
|---|--------|-------|------|----|----|
| f/2 medium | BEA_IDA_0071B | 62.6 ± 2.8 | 22.5 ± 0.4 | 7.7 ± 0.3 | 38.4 ± 1.1 |
| | BEA_IDA_0069B | 57.8 ± 0.11 | 21.3*1 | 7.8 ± 0.8 | 36.8 ± 0.1 |
| | BEA_IDA_0072B | 57.7 ± 0.1 | 21.2 ± 1.1 | 8.4 ± 0.9 | 36.8 ± 0.1 |
| | BEA_IDA_0070B | 57.7 ± 0.1 | 21.6 ± 1.2 | 7.8 ± 0.6 | 36.9 ± 0.1 |
| | Strain | mS/cm | ° C. | pH | ‰ |
| 0.5% Effluent Medium | BEA_IDA_0071B | 62.5 ± 2.6 | 22.5 ± 0.5 | 7.6 ± 02 | 38.2 ± 1.1 |
| | BEA_IDA_0069B | 57.5 ± 0.1 | 21.1 ± 0.9 | 8.4 ± 0.3 | 36.8 ± 0.1 |
| | BEA_IDA_0072B | 57.5 ± 0.1 | 21.1 ± 0.9 | 8.9 ± 0.3 | 36.7 ± 0.1 |
| | BEA_IDA_0070B | 57.5 ± 0.1 | 21.2 ± 0.9 | 8.6 ± 0.3 | 36.7 ± 0.1 |

TABLE 3

Composition range of the effluent used to prepare the nutrient medium by mixing
seawater (Mean ± SD, n = 6).

| Cations | | Anions | | Metals | | Other parameters | |
|---|---|---|---|---|---|---|---|
| Compound | mg/l | compound | mg/l | compound | mg/l | Parameter | Units |
| Calcium | 84.5 ± 15.5 | Bicarbonates | 17,531 ± 541 | Boron | 0.475 ± 0.125 | BOD5 | 2,270 ± 730 (mg/l) |
| Magnesium | 1.05 ± 0.95 | Carbonates | 1.05 ± 0.95 | Copper | 0.15 ± 0.05 | COD | 6,745 ± 255 (mg/l) |
| Potassium | 604 ± 104 | Chloride | 1,100 ± 600 | Iron | 4.64 ± 1.35 | pH | 8.35 ± 0.15 |
| Sodium | 553 ± 17 | Nitrate | 133 ± 3 | Manganese | 0.15 ± 005 | Conductivity | 25.45 ± 0.35 (mS/cm) |
| Ammonium | 4,239 ± 205 | Sulphate | 230 ± 130 | Mercury | 0.075 ± 0.025 | Salinity | 13.1 ± 0.1 (% o) |
|  |  | Orthophosphate | 525 ± 195 | Zinc | 0.2 ± 0.1 | Aerobic microorganisms | 42,500 ± 2,500 (cfu/ml) |
|  |  |  |  |  |  | CDOM | 431 ± 15 (PPB) |

TABLE 4

Nutrient composition, N/P quotient, bacterial activity, salinity, pH, conductivity, dry weight and CDOM of filtered
seawater, f/2 medium and the different effluent dilutions tested in this work (Mean ± SD, n = 6) Bold means the nutrient medium
selected to carry out the experiments, as a clean medium, f/2; and as an effluent medium, a dilution in seawater of 0.5%.

| | Ammonium (mg/l) | Nitrates (mg/l) | Orthophosphate (mg/l) | N/P | Bacterial activity (cfu/ml) | Salinity (%) | pH | Cd (mS/cm) | Dry weight (mg/l) | CDOM (PPB) |
|---|---|---|---|---|---|---|---|---|---|---|
| Filtered seawater | 1.1 ± 0.2 | 0 | 0 | | 0 | 38 | 7.9 | 64.35 | 0 | 0 |
| f/2 medium | 3.73 ± 6.53 | 80.73 ± 10.56 | 6.12 ± 1.18 | 14.7 ± 4.9 | 518 ± 238 | 36.9 ± 0.1 | 8.5 ± 0.4 | 57.7 ± 0.2 | 5.3 ± 0.8 | 30 ± 19 |
| 0.5% Effluent | 72.67 ± 15.12 | 33.63 ± 11.31 | 375 ± 1.07 | 31.3 ± 11.5 | 2,460 ± 659 | 36.8 ± 0.2 | 8.5 ± 0.4 | 57.6 ± 0.2 | 0.08 ± 0.01 | 73 ± 31 |
| 5% Effluent | 219 ± 57 | 62.5 ± 20.6 | 277 ± 12.9 | 11.1 ± 2.3 | 3,500 ± 3.400 | 37.4 ± 0.2 | 8.0 ± 04 | 56.0 ± 0.1 | 0.4 ± 0.02 | 150 ± 30 |
| 10% Effluent | 297.7 ± 126 | 70 ± 35.8 | 57.25 ± 19.3 | 6.44 ± 0.8 | 13,740 ± 9,630 | 36 ± 0.4 | 7.9 ± 0.3 | 54.6 ± 0.2 | 0.8 ± 0.04 | 300 ± 28 |
| 30% Effluent | 1,414 ± 137 | 81 ± 46.2 | 237.7 ± 87.6 | 6.3 ± 35 | 110,200 ± 109,290 | 32 ± 0.3 | 7.9 ± 0.3 | 54.4 ± 0.2 | 2.6 ± 0.1 | 742 ± 45 |
| 50% Effluent | 2,216 ± 362 | 114 ± 60.4 | 388.3 ± 101.4 | 60 ± 1.2 | 780,000 ± 643,000 | 27.5 ± 0.2 | 8.1 ± 0.2 | 48.3 ± 0.2 | 6.1 ± 12 | 900 ± 120 |
| 100% Effluent | 4,239 ± 205 | 133 ± 3 | 525 ± 195 | 8.3 ± 1.8 | 42,500 ± 2.500 | 13.2 ± 0.3 | 8.4 ± 0.2 | 25.4 ± 0.3 | 11.6 ± 1.8 | 431 ± 15 |

TABLE 5

Results (mean ± SD) of the different pan meters studied in f/2 medium and in 0.5% effluent medium for each of the
microalgal strains analysed. Values in bold mean that there is a significant difference between nutrient media (p <0.05).

| f/2 medium | IPS (g/l) | Production (g/l · d) | N Yield (mg/gB) | N removal (mg/l · d) | P Yield (mg/gB) | P removal (mg/l · d) | Fv/Fm | F0 | Chl a (mg/ml) | OD | CDOM (PPB) | Bacterial growth (cfu/ml · d) |
|---|---|---|---|---|---|---|---|---|---|---|---|---|
| BEA_IDA_0071B | 0.089 | 0.075 ± 0.024 | 78 ± 37 | 23.8 ± 11.3 | 4.8 ± 1.7 | 1.4 ± 0.5 | 0.542 ± 0.052 | 1,910 ± 602 | 0.08 ± 0.03 | 0.044 ± 0.019 | 19.0 ± 13.9 | 193 ± 137 |
| BEA_IDA_0069B | 0.053 | 0.027 ± 0.014 | 57.5 ± 28.8 | 10.1 ± 3.9 | 5.4 ± 1.5 | 1.0 ± 0.1 | 0.691 ± 0.035 | 12,683 ± 3,419 | 0.74 ± 0.14 | 0.126 ± 0.042 | 22.1 ± 8.2 | 66 ± 46 |
| BEA_IDA_0072B | 0.080 | 0.045 ± 0.011 | 25.6 ± 13.8 | 12.4 ± 3.8 | 2.5 ± 1.2 | 0.8 ± 0.4 | 0.756 ± 0.028 | 5,339 ± 1,668 | 0.36 ± 0.18 | 0.100 ± 0.035 | 45.9 ± 18.8 | 266 ± 180 |
| BEA_IDA_0070B | 0.053 | 0.009 ± 0.006 | 29.1 ± 14.2 | 5.8 ± 23 | 3.8 ± 1.6 | 1.1 ± 0.3 | 0.752 ± 0.055 | 11,162 ± 6.011 | 0.89 ± 0.33 | 0.112 ± 0.048 | 39.8 ± 11.0 | 133 ± 70 |

| 0.5% effluent medium | IPS (g/l) | Production (g/l · d) | N Yield (mg/gB) | N removal (mg/l · d) | P Yield (mg/gB) | P removal (mg/l · d) | Fv/Fm | F0 | Chl a (mg/ml) | OD | CDOM (PPB) | Bacterial growth (cfu/ml · d) |
|---|---|---|---|---|---|---|---|---|---|---|---|---|
| SEA_IDA_0071B | 0.089 | 0.073 ± 0.042 | 93.0 ± 47.0 | 24.9 ± 11.1 | 4.5 ± 2.0 | 1.2 ± 0.5 | 0.610 ± 0.065 | 3,344 ± 1,800 | 0.17 ± 0.10 | 0.051 ± 0.024 | 77.1 ± 15.2 | 133 ± 50 |
| BEA_IDA_0069B | 0.053 | 0.053 ± 0.016 | 53.3 ± 20.2 | 11.2 ± 0.6 | 4.1 ± 1.4 | 0.9 ± 0.3 | 0.712 ± 0.037 | 13.324 ± 3,740 | 0.83 ± 0.13 | 0.144 ± 0.072 | 79.6 ± 43.6 | 200 ± 75 |
| BEA_IDA_0072B | 0.086 | 0.131 ± 0.027 | 25.5 ± 16.3 | 12.1 ± 8.3 | 2.2 ± 0.3 | 1.1 ± 0.1 | 0.651 ± 0.155 | 11,281 ± 4,605 | 0.49 ± 0.17 | 0.157 ± 0.065 | 74.0 ± 60.9 | 200 ± 75 |

TABLE 5-continued

Results (mean ± SD) of the different pan meters studied in f/2 medium and in 0.5% effluent medium for each of the microalgal strains analysed. Values in bold mean that there is a significant difference between nutrient media (p <0.05).

| | | | | | | | | | | | |
|---|---|---|---|---|---|---|---|---|---|---|---|
| BEA_IDA_0070B | 0.053 | 0.019 ± 0.016 | 39.1 ± 5.5 | 6.9 ± 0.5 | 4.6 ± 1.1 | 0.8 ± 02 | 0.717 ± 0.058 | 18,694 ± 6,011 | 1.40 ± 0.32 | 0.174 ± 0.084 | 90.1 ± 45.9  100 ± 37 |

TABLE 6

Results of the microbiology analysis for the biomass in dry weight obtained in the experiments carried out for the different microalgal strains in f/2 medium and in 0.5% effluent medium.

| | BEA_IDA_0071B | | BEA_IDA_0069B | | BEA_IDA_0072B | | BEA_IDA_0070B | |
|---|---|---|---|---|---|---|---|---|
| Units (cfu/g) | f/2 | 0.5% effluent | f/2 | 0.5% effluent | f/2 | 0.5% effluent | f/2 | 0.5% effluent |
| Aerobic microorganisms | 500 | 4,500 | 740 | 11,000 | 1100 | 45,000 | 750 | 19,000 |
| Faecal coliforms | Absence | Absence | Absence | Absence | Absence | Absence | Absence | Absence |
| E. coli β-D-glucuronidase | Absence | Absence | Absence | Absence | Absence | Absence | Absence | Absence |
| Salmonella spp | Absence | Absence | Absence | Absence | Absence | Absence | Absence | Absence |
| Listeria monocytogenes | Absence | Absence | Absence | Absence | Absence | Absence | Absence | Absence |

TABLE 7

Results of heavy metal concentrations in the lyophilised biomass (DW) of the strain BEA_IDA_0071B cultured in f/2 medium and in 0.5% effluent medium.

| | Heavy metals (mg/kg DW) | | | |
|---|---|---|---|---|
| | Cd | Pb | Hg | Ar |
| f/2 medium | <0.02 | 0.31 ± 0.09 | <0.09 | 1.6 ± 0.3 |
| 0.5% effluent medium | <0.02 | 0.34 ± 0.10 | <0.09 | 2.3 ± 0.5 |

TABLE 8

Results of the fatty acid profiles for the different strains studied in the control f/2 medium and in the 0.5% effluent medium. There were no significant differences between the nutrient media (p >0.800).

| Fatty acid (%) | f/2 medium | | | | 0.5% effluent medium | | | |
|---|---|---|---|---|---|---|---|---|
| | BEA_IDA_0071B | BEA_IDA_0069B | BEA_IDA_0072B | BEA_IDA_0070B | BEA_IDA_0071B | BEA_IDA_0069B | BEA_IDA_0072B | BEA_IDA_0070B |
| 14:0 | 0.4 | 0.2 | 0.1 | 1.1 | 0.1 | 0.2 | 0.2 | 1.1 |
| 16:0 | 29.4 | 19.1 | 24.1 | 26.1 | 29.3 | 20.9 | 22.0 | 23.2 |
| 16:1n-7 | 1.5 | 0.6 | 1.0 | 8.5 | 1.6 | 0.4 | 2.0 | 5.1 |
| 18:0 | 0.9 | 0.9 | 2.3 | 4.2 | 0.8 | 0.7 | 3.1 | 3.6 |
| 18:1n-9 | 2.0 | 10.9 | 29.2 | 13.6 | 2.1 | 10.4 | 24.8 | 13.7 |
| 18:1n-7 | 0.9 | 3.7 | 3.8 | 8.8 | 1.2 | 3.9 | 5.7 | 14.1 |
| 18:2n-6 | 7.9 | 6.5 | 9.5 | 7.2 | 8.0 | 7.4 | 7.9 | 6.8 |
| 18:3n-6 | 0.4 | 0.8 | 0.4 | 0.4 | 0.4 | 0.4 | 0.3 | 0.3 |
| 18:3n-3 | 0.4 | 19.3 | 15.3 | 15.4 | 0.6 | 16.6 | 19.3 | 13.4 |
| 18:4n-3 | 0.2 | 5.4 | 1.0 | 0.3 | 0.3 | 4.2 | 0.8 | 0.6 |
| 20:0 | 0.1 | 0.2 | 0.2 | 3.9 | 0.1 | 0.0 | 0.2 | 1.9 |
| 20:1n-9 | 0.0 | 1.8 | 0.2 | 0.1 | 0.0 | 0.7 | 0.3 | 0.2 |
| 20:2n-6 | 1.4 | 0.3 | 0.1 | 0.2 | 1.3 | 0.9 | 0.3 | 0.2 |
| 20:3n-9 | 0.1 | 0.0 | 0.0 | 0.1 | 0.1 | 0.0 | 0.0 | 0.1 |
| 20:3n-6 | 2.0 | 0.1 | 0.1 | 0.1 | 2.2 | 0.4 | 0.2 | 0.2 |
| 20:4n-6 | 32.3 | 0.4 | 0.3 | 0.5 | 32.1 | 0.6 | 0.4 | 0.9 |
| 20:4n-3 | 0.0 | 1.1 | 0.3 | 0.1 | 0.1 | 1.6 | 0.2 | 0.1 |
| 20:5n-3 | 14.9 | 6.3 | 0.6 | 1.6 | 14.3 | 3.6 | 0.8 | 2.7 |
| 22:1n-11 | 0.1 | 0.2 | 0.2 | 0.1 | 0.1 | 0.7 | 0.3 | 0.1 |
| 22:1n-9 | 0.1 | 0.8 | 0.5 | 0.5 | 0.1 | 1.5 | 0.5 | 0.5 |
| 22:4n-6 | 0.1 | 0.3 | 0.1 | 0.1 | 0.1 | 1.2 | 0.3 | 0.1 |
| 22:5n-3 | 0.2 | 0.5 | 0.2 | 0.2 | 0.0 | 1.0 | 0.4 | 0.2 |
| 22:6n-3 | 0.2 | 1.3 | 0.9 | 1.8 | 0.3 | 2.1 | 1.5 | 1.5 |
| % SFA | 31.0 | 20.6 | 27.1 | 35.9 | 30.6 | 22.2 | 26.0 | 30.9 |
| % MUFA | 8.4 | 26.3 | 39.9 | 33.4 | 8.8 | 28.7 | 37.4 | 38.1 |
| % PUFA | 60.7 | 53.8 | 33.5 | 31.2 | 60.6 | 50.5 | 36.9 | 31.4 |

TABLE 8-continued

Results of the fatty acid profiles for the different strains studied in the control f/2
medium and in the 0.5% effluent medium. There were no significant differences between
the nutrient media (p >0.800).

| Fatty acid (%) | f/2 medium | | | | 0.5% effluent medium | | | |
|---|---|---|---|---|---|---|---|---|
| | BEA_IDA_0071B | BEA_IDA_0069B | BEA_IDA_0072B | BEA_IDA_0070B | BEA_IDA_0071B | BEA_IDA_0069B | BEA_IDA_0072B | BEA_IDA_0070B |
| n-6 PUFA | 44.0 | 8.4 | 10.6 | 8.5 | 44.2 | 10.8 | 9.4 | 8.5 |
| n-3 PUFA | 16.1 | 34.4 | 18.9 | 20.5 | 15.8 | 29.4 | 23.8 | 19.5 |
| n-3:n-6 | 0.4 | 4.1 | 1.8 | 2.4 | 0.4 | 2.7 | 2.5 | 2.3 |

The invention claimed is:

1. A method for producing biomass from a microalgae, comprising:
culturing the microalgae in an effluent diluted in seawater, wherein the microalgae is at least one of a strain of the genus *Nodularia*, a strain of the genus *Chrysoreinhardia*, a strain of the genus *Halochlorella*, or combinations thereof,
wherein, at the beginning of culturing, the diluted effluent exhibits:
concentrations of total nitrogen (N) in the range of 30-150 mg/l; and
concentrations of total phosphorus (P) in the range of 1-15 mg/l,
wherein the N/P quotient is in the range of 25-40.

2. The method according to claim 1, wherein the strain of the genus *Nodularia* is at least one of a strain of the species *Nodularia spumigena* or a strain of the species *Nodularia harveyana*, wherein the strain of the genus *Chrysoreinhardia* is a strain of the species *Chrysoreinhardia giraudii*, and wherein the strain of the genus *Halochlorella* is a strain of the species *Halochlorella rubescens*.

3. The method according to claim 2, wherein the strain of the species *Nodularia spumigena* is BEA_IDA_0069B, wherein the strain of the species *Nodularia harveyana* is BEA_IDA_0070B, wherein the strain of the species *Chrysoreinhardia giraudii* is BEA_IDA_0071B, and wherein the strain of the species *Halochlorella rubescens* is BEA_IDA_0072B.

4. The method according to claim 1, wherein the concentration of ammonium (N-NH$_4^+$) with respect to the concentration of total nitrogen (N) in the diluted effluent is at least 50%.

5. The method according to claim 1, wherein inoculation of the microalgae in the effluent diluted in seawater is carried out with at least 50 mg/l of dry biomass.

6. The method according to claim 1, further comprising:
harvesting the biomass from the microalgae by filtration.

7. The method according to claim 1, wherein the culturing is carried out in photobioreactors under outdoor environmental conditions.

8. The method according to claim 1, wherein the culturing is carried out under a mean irradiation of at least 1750 µmoles photons/m$^2$·s.

9. A method for bioremediating an effluent, comprising:
culturing a microalgae in the effluent diluted in seawater, wherein the microalgae is at least one of a strain of the genus *Nodularia*, a strain of the genus *Chrysoreinhardia*, a strain of the genus *Halochlorella*, or combinations thereof,
wherein, at the beginning of culturing, the diluted effluent exhibits:
concentrations of total nitrogen (N) in the range of 30-150 mg/l; and
concentrations of total phosphorus (P) in the range of 1-15 mg/l,
wherein the N/P quotient is in the range of 5-4025-40.

10. The method, according to claim 9, wherein the strain of the genus *Nodularia* is at least one of a strain of the species *Nodularia spumigena* or a strain of the species *Nodularia harveyana*, wherein the strain of the genus *Chrysoreinhardia* is a strain of the species *Chrysoreinhardia giraudii*, and wherein the strain of the genus *Halochlorella* is a strain of the species *Halochlorella rubescens*.

11. The method according to claim 10, wherein the strain of the species *Nodularia spumigena* is BEA_IDA_0069B, wherein the strain of the species *Nodularia harveyana* is BEA_IDA_0070B, wherein the strain of the species *Chrysoreinhardia giraudii* is BEA_IDA_0071B, and wherein the strain of the species *Halochlorella rubescens* is BEA_IDA_0072B.

12. The method according to claim 9, wherein the concentration of ammonium (N-NH$_4^+$) with respect to the concentration of total nitrogen (N) in the diluted effluent is at least 50%.

13. The method according to claim 9, wherein inoculation of the microalgae in effluent diluted in seawater is carried out with at least 50 mg/l of dry biomass.

14. The method according to claim 9, further comprising:
harvesting the biomass from the microalgae by filtration.

15. The method according to claim 9, wherein the culturing is carried out in photobioreactors under outdoor environmental conditions.

16. The method according to claim 9, wherein the culturing is carried out under a mean irradiation of at least 1750 µmoles photons/m$^2$·s.

17. A method for producing a processed material from microalgal biomass, comprising: (a) producing microalgal biomass according to the method of claim 1, and (b) producing a processed material from the microalgal biomass.

18. The method according to claim 17, wherein the processed material is selected from the group consisting of a fertiliser, pesticide, feed, feed for fish, biofuel, jet fuel, biodiesel, pigment, surfactant, cosmetic, pharmaceutical agent, nutraceutical product, prebiotic product, probiotic product, functional food, health supplement, and bioplastics.

19. A method for producing a biomass extract from a microalgae, comprising:
i) culturing the microalgae in an effluent diluted in seawater,
wherein the microalgae is at least one of a strain of the genus *Nodularia*, a strain of the genus *Chrysoreinhardia*, a strain of the genus *Halochlorella*, or combinations thereof, wherein, at the beginning of culturing, the diluted effluent exhibits:

concentrations of total nitrogen (N) in the range of 30-150 mg/l; and concentrations of total phosphorus (P) in the range of 1-15 mg/l, wherein the N/P quotient is in the range of 25-40;

ii) harvesting the biomass from the microalgae by filtration;

iii) subjecting the microalgal biomass to a cellular breakage method; and iv) obtaining the extract resulting from cellular breakage.

20. The method of claim 19, wherein the cellular breakage method is carried out with a system selected from the group consisting of a ball mill, a system delivering microwaves, and a system delivering a pulsed electric field.

\* \* \* \* \*